United States Patent
Honda et al.

(10) Patent No.: US 8,184,768 B2
(45) Date of Patent: May 22, 2012

(54) X-RAY CT APPARATUS AND METHOD FOR CONTROLLING X-RAY TUBE

(75) Inventors: Toyomasa Honda, Nasushiobara (JP); Shinsuke Tsukagoshi, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 12/841,464

(22) Filed: Jul. 22, 2010

(65) Prior Publication Data

US 2011/0019793 A1 Jan. 27, 2011

(30) Foreign Application Priority Data

Jul. 27, 2009 (JP) ................................. 2009-174177

(51) Int. Cl.
*A61B 6/00* (2006.01)
(52) U.S. Cl. ............................... 378/16; 378/8; 378/134
(58) Field of Classification Search ................ 378/8, 16, 378/134
See application file for complete search history.

(56) References Cited

U.S. PATENT DOCUMENTS

| | | | | |
|---|---|---|---|---|
| 4,160,906 A | * | 7/1979 | Daniels et al. | 378/97 |
| 4,685,118 A | * | 8/1987 | Furbee et al. | 378/114 |
| 4,748,649 A | * | 5/1988 | Griesmer et al. | 378/97 |
| 4,763,343 A | * | 8/1988 | Yanaki | 378/110 |
| 4,823,371 A | * | 4/1989 | Grady | 378/134 |
| 5,511,105 A | * | 4/1996 | Knott | 378/134 |
| H1627 H | * | 1/1997 | Broz et al. | 378/98.12 |
| 6,075,837 A | * | 6/2000 | Roos et al. | 378/98.2 |
| 6,322,248 B1 | * | 11/2001 | Yanagita et al. | 378/205 |
| 6,426,996 B1 | * | 7/2002 | Moribe et al. | 378/116 |
| 6,480,572 B2 | * | 11/2002 | Harris et al. | 378/136 |
| 6,507,639 B1 | * | 1/2003 | Popescu | 378/108 |
| 6,876,720 B2 | | 4/2005 | Tsuyuki | |
| 7,085,354 B2 | * | 8/2006 | Kanagami | 378/136 |
| 7,397,044 B2 | * | 7/2008 | Calderon et al. | 250/492.1 |
| 7,409,043 B2 | * | 8/2008 | Dunham et al. | 378/115 |
| 2002/0126798 A1 | * | 9/2002 | Harris et al. | 378/136 |
| 2003/0007593 A1 | * | 1/2003 | Heuscher et al. | 378/4 |
| 2003/0108149 A1 | * | 6/2003 | Tsuyuki | 378/54 |

FOREIGN PATENT DOCUMENTS

| | | |
|---|---|---|
| JP | 2006-516206 | 6/2006 |
| JP | 2007-324068 | 12/2007 |
| JP | 2009-11863 | 1/2009 |
| JP | 2009-158138 | 7/2009 |
| WO | WO 2004/061864 A2 | 7/2004 |

* cited by examiner

*Primary Examiner* — Alexander H Taningco
(74) *Attorney, Agent, or Firm* — Oblon, Spivak, McClelland, Maier & Neustadt, L.L.P.

(57) ABSTRACT

This embodiment is provided with a detector configured to detect an X-ray radiated from an X-ray tube, a reconstructing part configured to reconstruct an image from projection data based on the detection by the detector, an acquiring part configured to acquire a parameter indicating the status of a scan, a determining part configured to determine whether the parameter acquired by the acquiring part during the scan is included within a reference range, and a controller configured to change the size of a focal point of an electron beam to a different size depending on the determination result during the scan with reference to the result of the determination by the determining part.

21 Claims, 18 Drawing Sheets

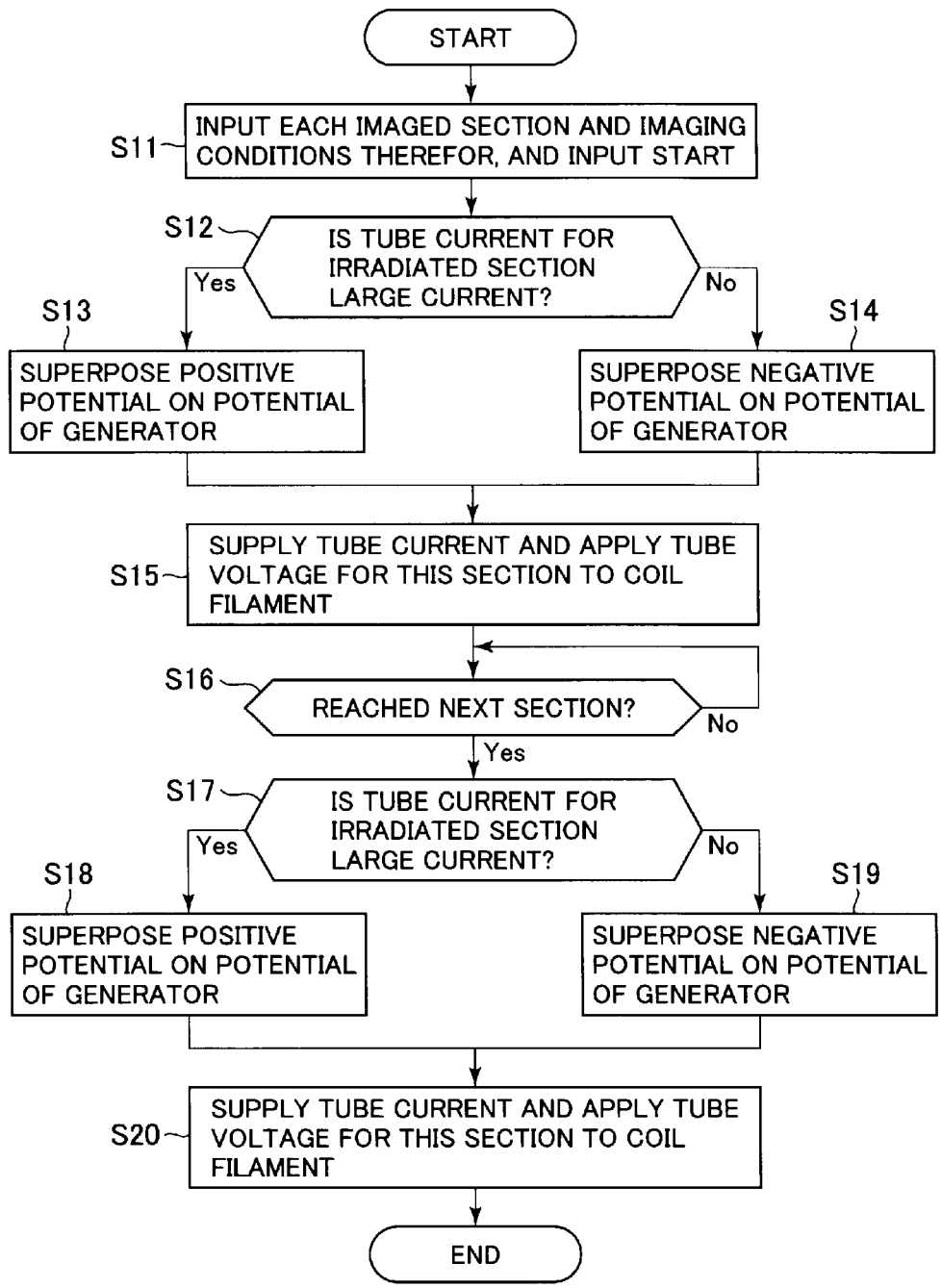

FIG.9
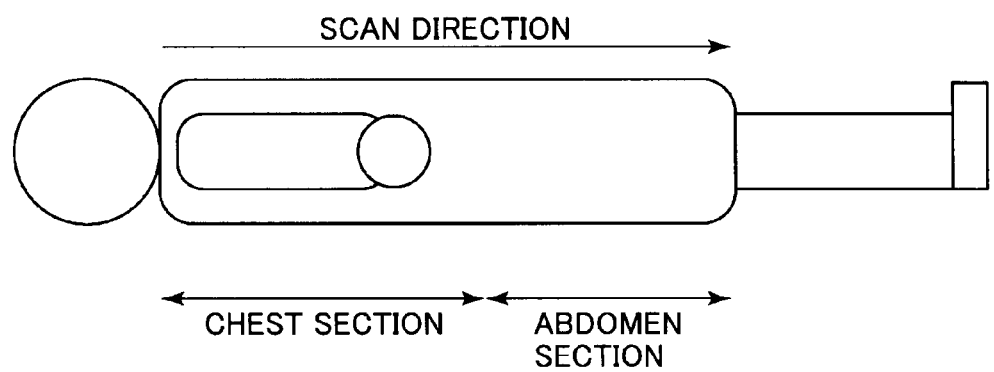
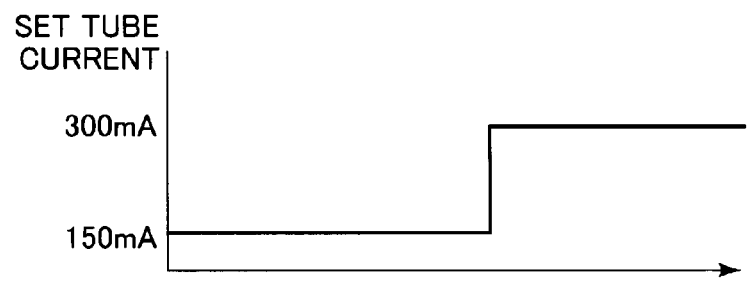

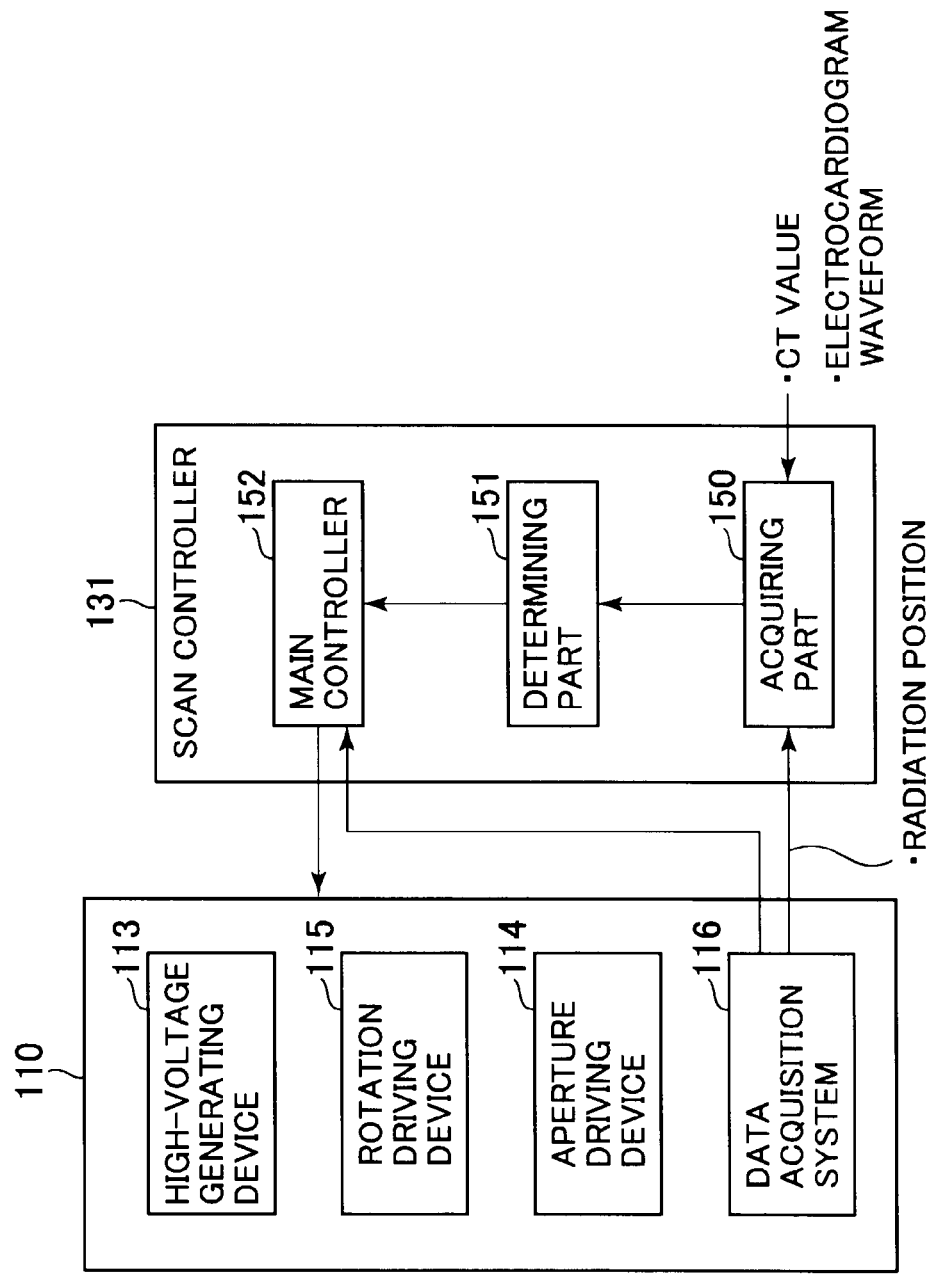

US 8,184,768 B2

X-RAY CT APPARATUS AND METHOD FOR CONTROLLING X-RAY TUBE

CROSS-REFERENCE TO RELATED APPLICATION

This application is based upon and claims the benefit of priority from Japanese Patent Application No. 2009-174177, filed on Jul. 27, 2009; the entire contents of which are incorporated herein by reference.

FIELD

Embodiments described herein relate generally to an X-ray CT apparatus configured to reconstruct an image from projection data of a subject obtained by radiating an X-ray.

BACKGROUND

An X-ray CT apparatus is an image diagnosis apparatus that irradiates, mainly, radiates an X-ray, detects transmission thereof through a subject, and reconstructs an image of the inside of the subject from projection data indicating the intensity of the radiation having been detected. The apparatus plays an important role in many medical practices including diagnosis of a disease and plan of treatment and operation. The X-ray CT apparatus irradiates a subject from multiple directions, and reconstructs one tomographic image from, for example, projection data for 360 degrees or projection data for 180 degrees plus a fan angle (the angle of a fan beam). Moreover, the apparatus reconstructs a volume image, which is a three-dimensional image, from projection data stacked by continuously moving a scan position in the direction of the body axis of the subject.

In recent years, as a method for imaging a subject with the X-ray CT apparatus, various methods have been proposed. One example of the methods is a real prep scan. In the real prep scan, the flow of a contrast agent into a slice of interest is detected in a prep scan at low doses and, when a sufficient amount of contrast agent flows into a region of interest, the scan is switched to a real scan. Another example of the methods is an ECG-gated scan. In the ECG-gated scan, electrocardiographic waveforms are acquired by an electrocardiograph and a scan aspect is changed in synchronization with appearance of a predetermined cardiac phase. Moreover, there is a method of changing a scan aspect for each site when collectively scanning a plurality of sites.

The scan aspects are all for switching imaging conditions during a scan. For example, the X-ray dose is switched between a prep scan and a real scan, or the X-ray dose is increased when a predetermined cardiac phase appears, or a tube current supplied to a coil filament of an X-ray tube is switched for each site.

In conventional techniques, an X-ray tube generates an X-ray by, in a state that a coil filament and an anode face each other, supplying a tube current and applying a high voltage to the coil filament so that thermo electrons are generated and radiated to the anode. This X-ray tube is generally provided with a large filament with a large number of windings and a small filament with a small number of windings.

With the small filament, it is possible to obtain a high-resolution image because the focal point of electrons radiated to the anode is small in size, but it takes time to scan. On the other hand, with the large filament, because the focal point of electrons radiated to the anode is large in size, it is possible to radiate an X-ray to a wide range at one time and scan in a shorter time, and it is also possible to obtain a low-noise image. However, it is impossible to obtain a high-resolution image. Thus, the X-ray tube is provided with the small filament and the large filament so that these two filaments are selectively used.

For switching from the small filament to the large filament or vice versa, that is, for changing a filament to which a tube current is supplied and a tube voltage is applied, there is a process of turning off supply of the tube current and application of the tube voltage to one of the filaments and then turning on supply of the tube current and application of the tube voltage to the other filament. Consequently, it takes much time to switch the filaments.

BRIEF DESCRIPTION OF THE DRAWINGS

FIG. 8 is a flow chart showing an operation of a change control of the size of a real focal point in the case of collectively scanning a plurality of sites.

FIG. 9 is a schematic view showing change of the size of a real focal point in accordance with change of an imaging site.

FIG. 17 is a block diagram describing a control operation relating to change of the size of a focal point by a scan controller.

DETAILED DESCRIPTION

Embodiments described hereinafter were made in consideration of the above circumstance, and an object thereof is to provide an X-ray CT apparatus capable of switching the size of the focal point of electrons radiated to an anode during a scan.

The embodiments are applied to an X-ray CT apparatus that reconstructs an image from projection data obtained in a scan by radiating and detecting an X-ray. This X-ray CT apparatus has an X-ray tube that radiates an X-ray. The X-ray tube has a filament, an anode, and generators. The generators are arranged so as to face each other across a path heading from the filament to the anode. The generators output an electric field or a magnetic field onto the path to focus an electron beam heading from the filament to the anode in accordance with the output.

Further, the X-ray CT apparatus is provided with: a detector configured to detect an X-ray radiated from the X-ray tube; a reconstructing part configured to reconstruct an image from projection data based on the detection by the detector; an acquiring part configured to acquire a parameter indicating the status of a scan, a determining part configured to determine whether the parameter acquired by the acquiring part during the scan is included within a reference range; and a controller configured to control the intensity of the output of the generators with reference to the result of the determination by the determining part to change the focal point size of the electron beam during the scan to a different size depending on the determination result.

Below, a preferable embodiment of an X-ray CT apparatus according to the present invention will be specifically described with reference to the drawings.

An X-ray CT apparatus is an apparatus that reconstructs an image from projection data obtained by scanning a subject. The scan by the X-ray CT apparatus is radiation of an X-ray and detection of the transmitted X-ray. The X-ray CT apparatus is equipped with an X-ray tube 1, and radiates an X-ray by the X-ray tube 1.

Figure 1:
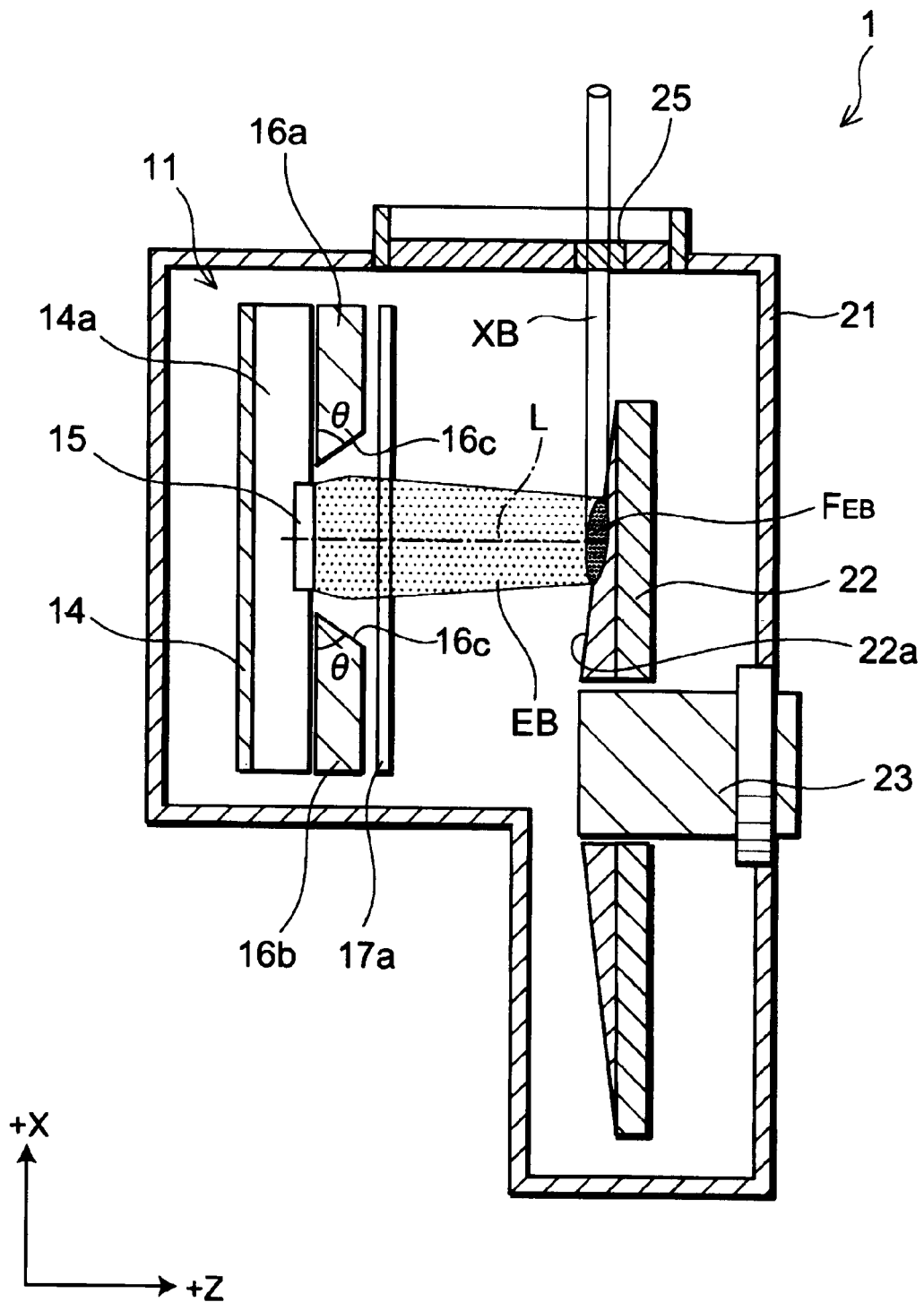
FIG. 1 is a cross-sectional view of an X-ray tube cut along an X-ray radiation axis.
Figure 2:
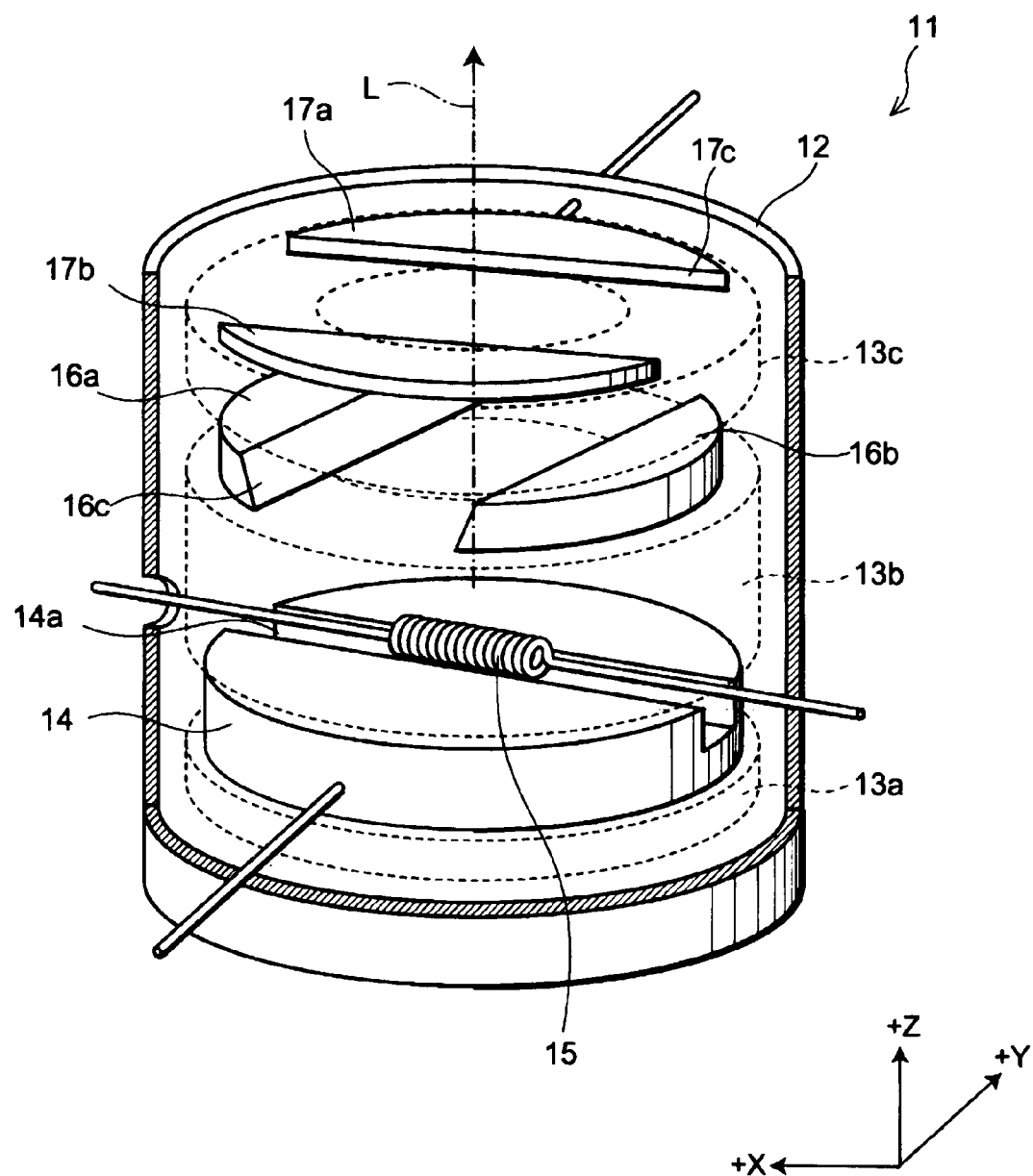
FIG. 2 is a cross-sectional perspective view of an electron gun installed within the X-ray tube, cut along an electron emission direction.
Figure 3A:
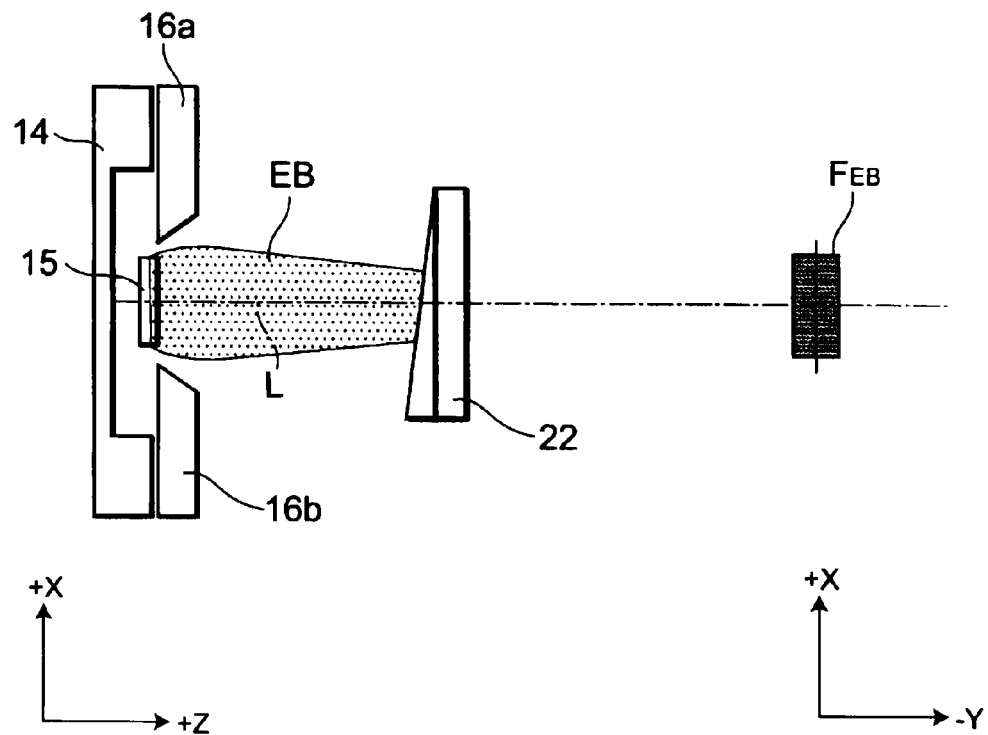
FIGS. 3A-3C are cross-sectional views of the X-ray tube cut along the electron emission direction, showing various aspects of electrons emitted from the electron gun.
Figure 3B:
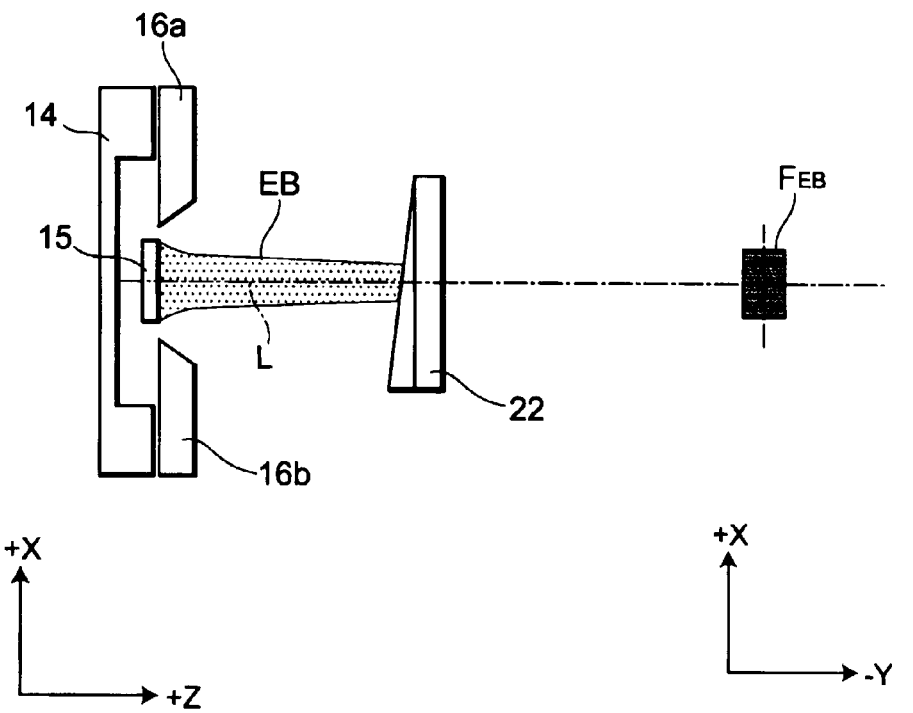
Figure 3C:
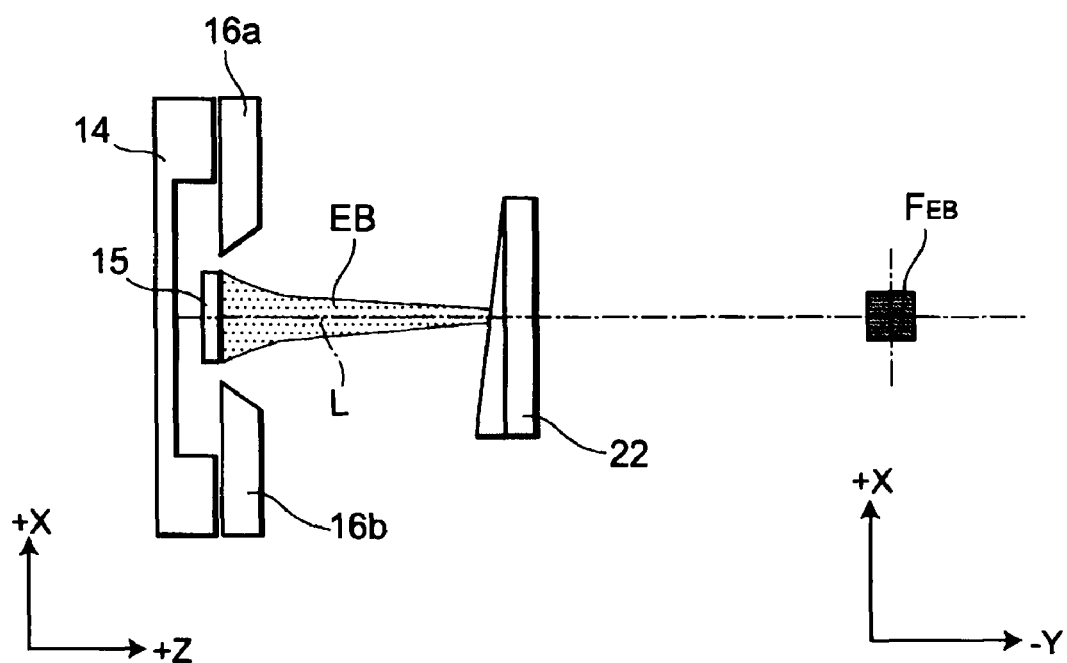

Firstly, the X-ray tube 1 will be described based on FIGS. 1, 2 and 3A-3C. FIG. 1 is a cross-sectional view of the X-ray tube 1 cut along a radiation axis of the X-ray. FIG. 2 is a cross-sectional perspective view of an electron gun installed within the X-ray tube 1, cut along an emission direction of electrons. FIGS. 3A-3C are cross-sectional views of the X-ray tube 1 cut along the emission direction of electrons, showing various aspects of electrons emitted from the electron gun.

The X-ray tube 1 receives supply of a filament heating current and application of a high voltage to generate an X-ray. As shown in FIG. 1, this X-ray tube 1 is provided with an electron gun 11 that has a coil filament 15 emitting thermo electrons when electricity is flown therethrough, and an anode 22 that radiates an X-ray when irradiated with the electrons emitted by the coil filament 15. The electron gun 11 and the anode 22 are sealed within a vacuum shield chamber 21.

The electron gun 11 has a cylindrical shape with one end open.

On the perpendicular line (the −z-axis direction) extended down from the opening to the bottom along the axis, the coil filament 15 is placed. Upon supply of a filament heating current and application of a high voltage to the coil filament 15, the electron gun 11 radiates electrons from the opening onto a path L in the +z-axis direction.

The anode 22 is formed in one body with a rotation shaft 23 extending in the z-axis direction, and arranged on the path L connecting the coil filament 15 and the opening. This anode 22 emits an X-ray in a direction orthogonal to the rotation shaft 23 when the surface thereof on the path L is irradiated with the electrons emitted from the electron gun 11.

Therefore, the shape of the anode 22 is a truncated cone with an upper surface facing in the −z-axis direction, and the normal of a side surface 22a corresponding to the surface of the cone is tilted about 6-8 degrees, for example. Moreover, the rotation shaft 23 is extended outside the vacuum shield chamber 21, and rotated by an external driving mechanism (not shown). The central axis of the rotation shaft 23 is off the electron path L connecting the coil filament 15 and the opening in a predetermined direction (the −x-axis direction). Therefore, the electrons are radiated to the side surface 22a, which is a tilted surface of the anode 22. At least the side surface 22a of the anode 22, to which the electrons are radiated, is made of tungsten, for example.

The off-direction shall be a direction in which the coil filament 15 and a groove 14a described later extend.

In a position of the vacuum shield chamber 21, through which the X-ray radiated from the anode 22 passes, a window 25 made of a beryllium film is formed. The X-ray is taken outside the X-ray tube 1 through this window 25.

As shown in FIG. 2, in the X-ray tube 1, the electron gun 11 houses an insulating block 13a, a Wehnelt electrode 14, the coil filament 15, an insulating block 13b, a pair of X electrodes (first electrode members) 16a and 16b (also generically referred to as "X electrodes 16" hereinafter), an insulating block 13c, and a pair of Y electrodes (second electrode members) 17a and 17b (also generically referred to as "Y electrodes 17" hereinafter) arranged in this order from the bottom toward the opening of a shield 12 as a housing.

The shield 12 is made of a conductive material such as metal or alloy. The insulating block 13a is a disk-shaped member made of an insulation material, and the central axis thereof coincides with the central axis of the shield 12. The insulating block 13a holds the Wehnelt electrode 14 and insulates the Wehnelt electrode 14 from the shield 12.

The Wehnelt electrode 14 is a disk-shaped member made of nonmagnetic metal such as stainless steel. On a surface of the Wehnelt electrode 14 on the side of the opening of the shield 12, the groove 14a extending in a direction orthogonal to the axial direction of the shield 12. The central axis of the Wehnelt electrode 14 coincides with the central axis of the shield 12.

The coil filament 15 is a filament wounded like a spiral and extended in the same direction as the groove 14a. The coil filament 15 is made of, for example, tungsten and radiates thermo electrons when electricity is flown therethrough. The coil filament 15 is half housed in the groove 14a, but is not in contact with the Wehnelt electrode 14.

The insulating blocks 13b and 13c are ring-shaped members made of an insulation material, and the central axes thereof coincide with the central axis of the shield 12. The thicknesses of the insulating blocks 13b and 13c are each 1 mm or less, for example. The insulating block 13b holds the X electrodes 16 and insulates the X electrodes 16 from the Wehnelt electrode 14. The insulating block 13c holds the Y electrodes 17 and insulates the Y electrodes 17 from the X electrodes 16.

The X electrodes 16a and 16b are placed opposite to each other across the path L and arranged along the x-direction. The distance between the X electrodes 16a and 16b is longer than the longitudinal size of the coil filament 15. Moreover, the Y electrodes 17a and 17b are placed opposite to each other across the path L and arranged along the y-direction orthogonal to both the x-direction and the z-direction.

The X electrodes 16 are generators composed of a so-called electrode pair. When voltage is applied, an electric field is generated between the X electrodes 16a and 16b. The X electrodes 16 are made of nonmagnetic metal such as stainless steel. Moreover, the X electrodes 16 have the same shapes. The shape of each of the X electrodes 16 is part of a circular disk around one point on the path L, and the chord thereof extends in the y-direction. Moreover, end surfaces 16c facing the path L of the X electrodes 16 are tilted with respect to the z-direction so as to widen on the +z-direction side. That is to say, the end surfaces 16c are tiled with respect to a direction in which the path L extends so that a distance between parts closer to the anode 22 is larger than a distance between parts closer to the coil filament 15 in the X electrodes 16. A tilt angle θ (refer to FIG. 1) of each of the end surfaces 16c with respect to the x-direction is, for example, within the range of 50-80 degrees and is, for example, 70 degrees.

The Y electrodes 17 are generators composed of a so-called electrode pair. When voltage is applied, an electric field is generated between the Y electrodes 17a and 17b. The Y electrodes 17 are made of nonmagnetic metal such as stainless steel. The Y electrodes 17 have the same shapes. The shape is part of a circular disk around one point on the path L, and the chord thereof extends in the x-direction. The thickness of each of the Y electrodes 17 is less than the thickness of each of the X electrodes 16. End surfaces 17c of the Y electrodes 17 facing the path L are parallel to the z-direction. Moreover, the distance between the Y electrodes 17a and 17b is, for example, about ten times the diameter of the coil filament 15.

To the Wehnelt electrode 14, the X electrodes 16a and 16b, and the Y electrodes 17a and 17b, an electric potential is applied from outside the X-ray tube 1. Moreover, to the coil filament 15, electric power is supplied from outside the X-ray tube 1. The X electrodes 16a and 16b and the Y electrodes 17a and 17b are insulated from each other, respectively, and the electric potentials thereof can be controlled independently from each other.

Next, an operation of the X-ray tube 1 configured as described above will be explained based on FIG. 3. Firstly, a vacuum is created inside the vacuum shield chamber 21. Next, between the anode 22 and the Wehnelt electrode 14, voltage is applied to make the Wehnelt electrode 14 a negative electrode and make the anode 22 a positive electrode. For example, a ground potential is applied to the anode 22, and an electric potential of −150 kV is applied to the Wehnelt electrode 14. Moreover, a ground potential is applied to the shield 12.

Consequently, an electric field heading from the Wehnelt electrode 14 to the anode 22 is generated inside the vacuum shield chamber 21.

Further, the electric potential of the coil filament 15 is slightly more positive than the electric potential of the Wehnelt electrode 14, for example, −140 kV. The rotation shaft 23 is rotated from outside the X-ray tube 1 to rotate the anode 22.

In this state, electric power is supplied from outside the X-ray tube 1 to the coil filament 15 and flown therethrough. Consequently, the coil filament 15 is heated to emit thermo electrons. The emitted electrons contract due to the lens effect by the Wehnelt electrode 14, and form an electron beam EB along the path L to be radiated to the side surface 22a of the anode 22.

A region to which the electron beam EB is radiated on the side surface 22a of the anode 22 is a real focal point $F_{EB}$. The real focal point $F_{EB}$ has such a shape that the shape of the coil filament 15 is reduced. At this moment, by rotating the anode 22, a focal point burn on the anode 22 is prevented.

Consequently, the anode 22 radiates the X-ray from a part corresponding to the real focal point $F_{EB}$. The X-ray reaches the window 25, and is transmitted through the window 25 and radiated outside the X-ray tube 1. Thus, the X-ray tube 1 is used as an X-ray source of the X-ray CT apparatus.

By applying an electric potential to each of the X electrodes 16a and 16b and the Y electrodes 17a and 17b, the X-ray tube 1 can form a static electric field, control the trajectory of the electron beam EB, and control the size of the real focal point $F_{EB}$.

To be specific, a reference potential of each of the X electrodes 16 and the Y electrodes 17 is set to be equal to the electric potential of the Wehnelt electrode 14. Then, an electric potential within about several kV is superposed on the reference potential.

FIG. 3B shows a reference case in which the electric potentials of the X electrodes 16a and 16b are equal to the electric potential of the Wehnelt electrode 14. For example, the same positive potential is superposed on both the electric potentials of the X electrodes 16a and 16b to be +2 kV with respect to the electric potential of the Wehnelt electrode 14. Then, as shown in FIG. 3A, it is possible to increase the beam diameter of the electron beam EB in the x-direction, and it is possible to increase the size of the real focal point $F_{EB}$ in the x-direction.

On the contrary, the same negative potential is superposed on both the electric potentials of the X electrodes 16a and 16b to become −2 kV with respect to the electric potential of the Wehnelt electrode 14.

Then, as shown in FIG. 3C, it is possible to decrease the beam diameter of the electron beam EB in the x-direction, and it is possible to decrease the size of the real focal point $F_{EB}$ in the x-direction.

In a like manner, by controlling the electric potentials of the Y electrodes 17, it is possible to control the size in the y-direction of the real focal point $F_{EB}$. That is to say, in a like manner, by superposing the same positive potential on the electric potentials of the Y electrodes 17a and 17b, it is possible to increase the size in the y-direction of the real focal point $F_{EB}$. In a like manner, by superposing the same negative potential on the electric potentials of the Y electrodes 17a and 17b, it is possible to decrease the size in the y-direction of the real focal point $F_{EB}$.

Figure 4:
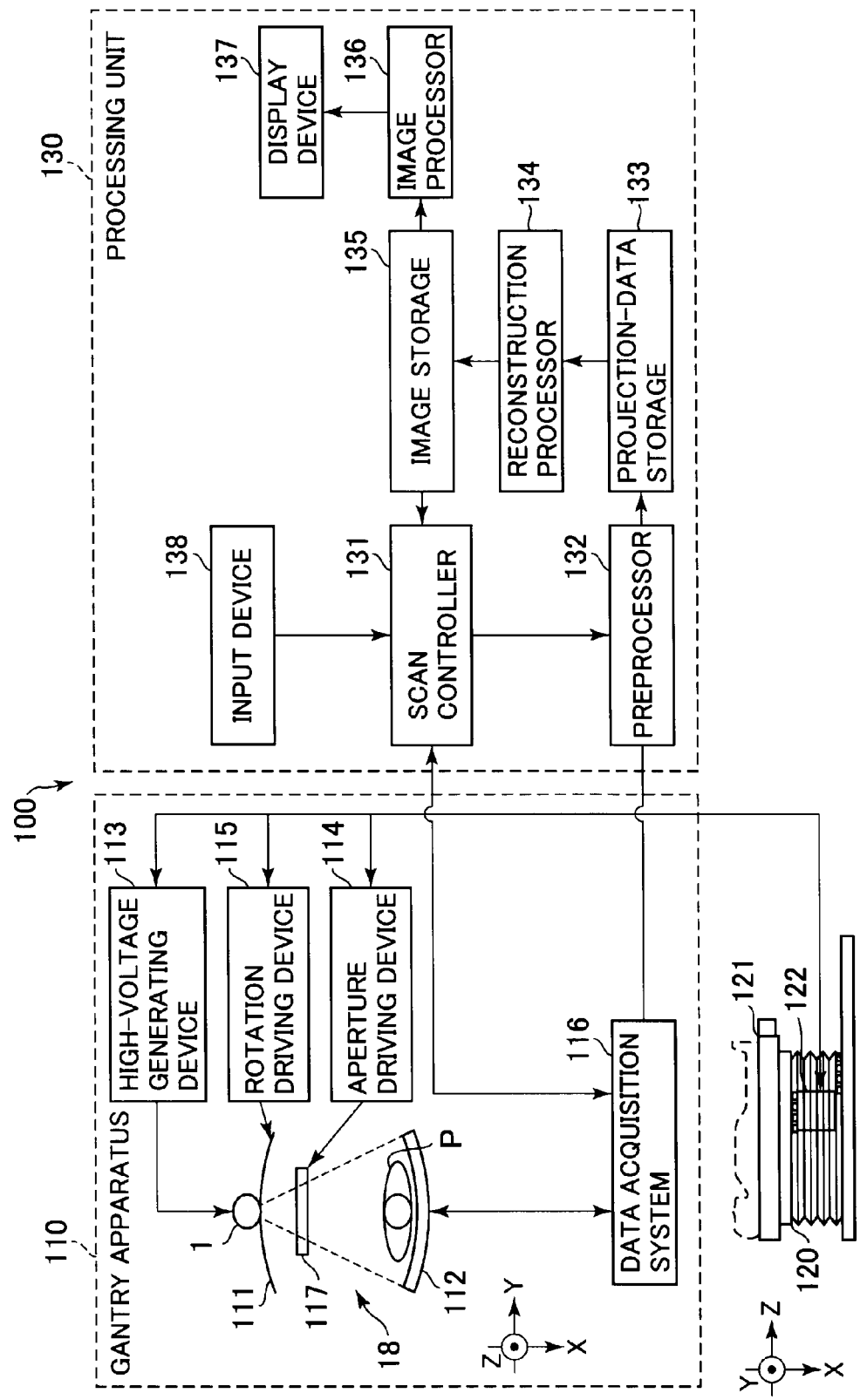
FIG. 4 is a block diagram showing a configuration of an X-ray CT apparatus equipped with the X-ray tube.

FIG. 4 is a block diagram showing a configuration of an X-ray CT apparatus 100 equipped with the X-ray tube 1.

The X-ray CT apparatus is provided with a gantry apparatus 110, a couch apparatus 120, and a processing unit 130. The gantry apparatus 110 and the couch apparatus 120 are connected by a signal line so as to be controllable by the processing unit 130.

The gantry apparatus 110 is an apparatus configured to irradiate with majorly an X-ray and detect the radiation transmitted through a subject. This apparatus has an aperture. Within the gantry apparatus 110, a rotating gantry 111 called a gantry is housed. The X-ray tube 1 is mounted on the rotating gantry 111 so as to be paired with a detector 112. The X-ray tube 1 and the detector 112 are mounted so as to face across the aperture of the rotating gantry 111. Moreover, within the gantry apparatus 110, a high-voltage generating device 113 and an aperture driving device 114 are arranged in pair with the X-ray tube 1, a rotation driving device 115 is arranged in pair with the rotating gantry 111, and a data acquisition system 116 is arranged in pair with the detector 112.

The rotating gantry 111 is driven by the rotation driving device 115 to rotate about the aperture. The high-voltage generating device 113 performs supply of a heating current and application of a high voltage to the coil filament 15 of the X-ray tube 1, and application of voltage to the X electrodes 16, the Y electrodes 17 and the Wehnelt electrode 14, separately. As this high-voltage generating device 113, a high-frequency inverter type is applied. The high-frequency inverter type rectifies an alternating current of 50/60 Hz to a direct current, converts the direct current to a high-frequency alternating current of several kHz or more, boosts and rectifies the current again, and then applies.

The aperture driving device 114 varies the irradiation field shape of a collimator 117 placed between the X-ray tube 1 and the detector 112, thereby narrowing down the generated radiation into a fan-beam shape or a cone-beam shape.

The detector 112 is provided with multiple rows and multiple channels of radiation detecting elements to detect radiation transmitted through a subject P and output the detected data (genuine data) as electric current signals. As the radiation detecting elements, the indirect conversion type that converts an X-ray into light with a phosphor such as a scintillator and then converts the light into electric charges with a photoelectric conversion element such as a photodiode, and the direct conversion type that utilizes photoconductive phenomenon, which is generation of electron-hole pairs by the X-ray and movement thereof to the electrode within a semiconductor, are mainly used.

The data acquisition system 116 is provided with an I-V convertor, an integrator, a preamplifier, and an A/D convertor for each of the radiation detecting elements. The data acquisition system 16 converts the electric current signals outputted from the respective radiation detecting elements into voltage signals, periodically integrates and amplifies the voltage signals in synchronization with a radiation period, and converts into digital signals. The data acquisition system 116 outputs the detected data converted into the digital signals to the processing unit 130 via the signal line.

On the upper surface of the base of the couch apparatus 120, a couch top 121 is mounted. On the couch top 121, the subject P is laid.

The couch top 121 can be driven by a couch driving device 122 to move in the direction of the aperture axis at a predetermined speed.

When rotation of the rotating gantry 111 and movement of the couch top 121 are simultaneously executed, movement of the couch top 121 and movement of the X-ray tube 1 and the detector 112 form a helical shape relative to each other. Thus, a helical scan is executed.

Moreover, by rotation of the rotating gantry 111 while stoppage of the couch top 121, a conventional scan or a dynamic scan is executed.

The processing unit 130 is provided with a scan controller 131, a preprocessor 132, a projection data storage 133, a reconstruction processor 134, an image storage 135, a display device 137, and an input device 138.

The display device 137 is a monitor such as a CRT or a liquid crystal display, and displays a reconstructed image of the inside of the subject P. The input device 138 is an input interface such as a keyboard, a mouse and a trackball. On the input interface, the operator performs input of imaging conditions, press of a start button, and so on.

The scan controller 131 controls a scan in accordance with the imaging conditions inputted by using the input device 138. The imaging conditions include a whole imaging range of a subject, a range of each of sections divided in the whole imaging range, a helical pitch (HP), a rotation speed, a tube voltage (kV), a tube current (mA), the size of the real focal point $F_{EB}$, and so on.

As the scan control, various control signals are outputted at predetermined moments to the high-voltage generating device 113, the rotation driving device 115, the data acquisition system 116, the aperture driving device 114, the couch driving device 122, the preprocessor 132 and the data acquisition system 134, whereby rotation of the rotating gantry, movement of the couch, the dose of the X-ray radiated by the X-ray tube 1, the size of the real focal point $F_{EB}$ emitted within the X-ray tube 1, the preprocessing of the projection data, and reconstruction of an image are controlled.

To be specific, in the control of the size of the real focal point $F_{EB}$ of electrons emitted to the anode 22 of the X-ray tube 1, the scan controller 131 superposes the same positive potential on the electric potentials of both the X electrodes 16a and 16b to make the real focal point $F_{EB}$ large-size. For example, the scan controller 131 superposes a positive potential on the electric potentials of both the X electrodes to become +2 kV with respect to the electric potential of the Wehnelt electrode 14. A like process is executed on the Y electrodes.

On the other hand, for making the real focal point $F_{EB}$ small-size, the scan controller 131 superposes the same negative potential on the electric potentials of both the X electrodes 16a and 16b. For example, the scan controller 131 superposes a negative potential on the electric potentials of both the potentials of the X electrodes to become −2 kV with respect to the electric potential of the Wehnelt electrode 14. A like process is executed on the Y electrodes.

In the control of the electric potentials of the X electrodes and Y electrodes, the scan controller 131 outputs a control signal that controls an electric potential to the high-voltage generating device 113, and the high-voltage generating device 113 gives an electric potential according to the control signal.

The preprocessor 132 executes sensitivity correction for correcting the intensity of an X-ray on the genuine data, and outputs projection data PD to the projection data storage 133. Into the projection data storage 133, projection data outputted from the preprocessor 132 is stored. Each projection data is provided with a view number. The view number indicates an angle at which an X-ray is radiated. For example, in the X-ray CT apparatus, when the X-ray tube 1 radiates an X-ray 900 times while the rotating gantry rotates once, the X-ray radiation angle is divided into 360/900, and a view number is given in accordance with the division.

The reconstruction processor 134 reconstructs an image within the subject P by back projection of the projection data. By a reconstruction process by image reconstruction algorithm typified by the Feldkamp method, this reconstruction processor 134 executes back projection of the projection data read out from the projection data storage 133, and reconstructs the inside of the subject P as image data.

The reconstructed image data is inputted and stored in the image storage 135.

The image processor 136 executes various kinds of image processing such a scan conversion process for converting into a video format of orthogonal coordinate system on the image data stored in the image storage 135, and generates a display image. The display device 137 displays the display image generated by the image processor 136.

FIG. 17 is a block diagram describing a control operation relating to change of the size of a focal point by the scan controller.

The scan controller 131 includes an acquiring part 150, a determining part 151, and a main controller 152. In accordance with the operation of each of these parts, the main controller 152 outputs a control signal to each of the parts (the high-voltage generating device 113, the rotation driving device 115, the data acquisition system 116, the aperture driving device 114, and so on) of the gantry apparatus 110, thereby controlling the operation of each of the parts of the gantry apparatus 110.

The acquiring part 150 acquires parameters showing the status of a scan. The status of a scan includes various statuses relating to a scan by radiation and detection of an X-ray. For example, the status of imaging based on the result of scan, the various statuses anticipated to influence on imaging when starting a scan, the status relating to an object to scan, and so on are included. Values are set for these scan statuses and given as parameters.

To be specific, examples of the parameters showing the scan status are a CT value described later with reference to FIGS. 5-7, an imaging position described later with reference to FIGS. 8 and 9, a value relating to an electrocardiographic waveform described later with reference to FIGS. 10-12, and an imaging view number described later with reference to FIGS. 13 and 14.

The acquiring part 150 acquires the various kinds of parameters described above. For example, the acquiring part 150 acquires the CT value from the image storage 150, and acquires the electrocardiographic waveform from an electrocardiograph 140 shown in FIG. 10. Moreover, the acquiring part 150 acquires a radiation position and the imaging view number from the data acquisition system 116.

The determining part 151 determines whether the parameter acquired by the acquiring part 150 during a scan is included in a reference range. The determining part 151 stores this reference range in advance, or stores a reference range inputted by the input device 138.

Then, the determining part 151 reads out the parameter from the acquiring part 150, and compares the parameter having been read out with the reference range. The determining part 151 determines based on the result of the comparison whether the parameter is within the reference range or out of the reference range, and outputs the result of the determination to the main controller 152.

Figure 6:
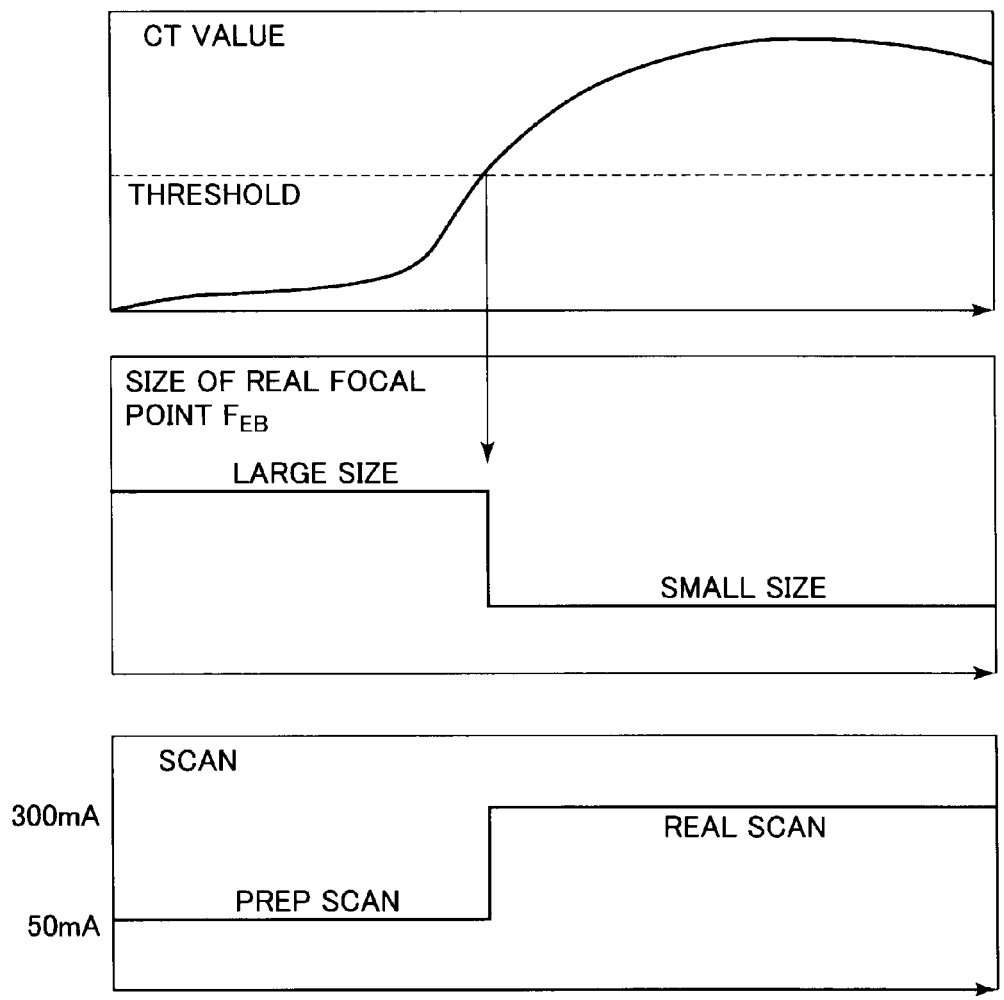
FIG. 6 is a schematic view showing change of a scan aspect based on a CT value and the size of a real focal point during the scan.

An example of the reference range is a range of values above a threshold as shown in FIG. 6. In this case, the reference range is defined by a threshold of the CT value, and the determining part 151 determines whether a parameter given as the CT value is beyond this threshold. Moreover, an example of the reference range is a range of imaging positions such as a chest section and an abdomen section shown in FIG. 9. In this case, the determining part 151 determines whether the parameter given as the imaging position is included in the chest section or the abdomen section. Moreover, an example of the reference range is a view number of whether the number of times of X-ray radiation is an even number or an add number. In this case, the determining part 151 determines whether the parameter given as the number of times of X-ray radiation is even or odd. The determining part 151 outputs a determination signal representing whether the number of times is included in the reference range to the main controller 152.

Other than the aforementioned control operation, the main controller 152 refers to the determination result of the determining part 151 to execute control of the output intensity of the generators, thereby changing the focal point size of the electron beam to a different size depending on the determination result of the determining part 151 during a scan. The determination result of the determining part 151 is, for example, whether the parameter is included within the aforementioned reference range. A control signal indicating the determination result is inputted by the determining part 151. The determining part 151 may output at all times, or may output at a moment that the determination result is changed. When the determination result is changed, the parameter is included within the reference range or out of the reference range. The main controller 152 changes the focal point size from a large size to a small size when the parameter is included within the reference range, and changes the focal point size from a small size to a large size in a case that the parameter is out of the reference range.

The generators are arranged so as to face each other across a path heading from the coil filament 15 to the anode 22. The generators include the X electrodes 16, the Y electrodes 17, and a device that supplies electric power to both the electrodes. Thus, the generators generate an electric field or a magnetic field. The generators output the electric field or magnetic field onto this path, thereby focusing an electron beam EB heading from the coil filament 15 to the anode 22 in accordance with the output. The output intensity of the generators is, for example, the magnitude of a tube current and/or the magnitude of a tube voltage. The main controller 152 changes the magnitude of the tube current and/or the magnitude of the tube voltage. The main controller 152 thus controls the output intensity, thereby changing the focal point size of the electron beam.

(Related Operation)

Although only change of the focal point size has been described as the operation of the main controller 152, the main controller 152 is not limited to separated execution of the change of the focal point size, but may accompany another operation. For example, in a case that the parameter is the CT value of an image, the main controller 152 changes the focal point size, and also continuously switches a scan between a prep scan and a real scan based on the CT value. To be specific, when the CT value exceeds a threshold, the main controller 152 switches the scan from a prep scan to a real scan, and also changes the focal point size from a large size to a small size. Moreover, when changing the focal point size from a large size to a small size, the main controller 152 increases the tube current of the X-ray tube. Although the tube current decreases when the focal point size is changed from a large size to a small size, the tube current is increased because the scan shifts from a prep scan to a real scan. However, since the focal point size is not kept to a large size but changed to a small size, the tube current decreases as compared with in a normal real scan. As a whole, the tube current increases in accordance with shift to a real scan.

For example, in a case that a parameter is a value indicating a radiation position of an X-ray to a subject and a reference range is a positional section by dividing an X-ray radiation range, the main controller 152 continuously changes an X-ray radiation position within the radiation range, and also changes the focal point size for each section that the X-ray radiation position reaches. Moreover, in a case that not only the X-ray radiation range is divided into sections but also a tube current for each section is set, the main controller 152 changes the focal point size in accordance with the tube current for the section that the X-ray radiation position reaches, and then changes the tube current.

Further, for example, in a case that a parameter is a value relating to an electrocardiographic waveform and a reference range is a range representing that the electrocardiographic waveform is a specific waveform, the main controller 152 changes the focal point size in synchronization with appearance of the specific waveform from waveforms outputted from an electrocardiograph. To be specific, the main controller 152 changes the focal point size from a large size to a small size in synchronization with appearance of a waveform representing diastasis, and changes the focal point size from a small size to a large size in synchronization with appearance of a waveform representing a heartbeat.

Further, for example, in a case that a parameter is a value representing a view in which the X-ray tube radiates an X-ray, the main controller 152 changes the focal point size for each view in which the X-ray tube radiates the X-ray. To be specific, the main controller 152 alternately changes between a focal point size of large size and a focal point size of small size every time the view changes.

(Focal Point Size)

The change of the focal point size has already been described above with reference to FIGS. 1-3. A large size and a small size are given as focal point sizes, and the respective focal point sizes are stored in advance. To change the focal point size to the large size, a control signal to make the focal point large-size is outputted. To change the focal point size to the small size, a control signal to make the focal point small-size is outputted. Two focal point sizes including the large and small sizes will be described hereinafter. However, instead of setting the two, it is also possible to set three sizes including large, middle and small sizes, or it is also possible to set four or more sizes. In these cases, a plurality of reference ranges will exist. The determining part 151 determines a reference range in which a parameter is included from among the plurality of reference ranges.

In accordance with the result of the determination, for example, the main controller 152 selects a focal point size B1 when the parameter is included in a reference range A1, selects a focal point size B2 when the parameter is included in a reference range A2, and selects a focal point size B3 when the parameter is included in a reference range A3. The main controller 152 thus selects a corresponding focal point size, and outputs a control signal to each part of the gantry apparatus 110 so as to change the focal point size to the selected one.

The main controller 152 changes the focal point size of the electron beam to a different size depending on the result of the determination by the determining part 151. That is to say, the focal point size of the electron beam is different before and after the change.

For example, a focal point size having been large-size before the change becomes small-size after the change, or vice versa.

The main controller 152 executes the change of the focal point size during a scan. The term "during a scan" includes "while keeping a state that the X-ray CT apparatus 10 is operating." In this state, the focal point size is changed. For example, the focal point size is changed by force of the electric field or magnetic field outputted by the generators while the operation of radiating and detecting an X-ray is continued.

(Fine-Tuning)

The main controller 152 is capable of controlling the focal point size of the electron beam EB by the function of the generators described above, and is also capable of controlling the size to be constant. However, the change of the focal point size described above does not refer to such fine-tuning but refers to more largely increasing or decreasing the focal point size. Simple fine-tuning is performed by controlling the focal point size, but is distinguished from the change of the focal point size itself.

However, this embodiment does not exclude the possibility of the fine-tuning of the focal point size. The main controller 152 may be configured to execute the aforementioned change of the focal point size and also execute fine-tuning control of the focal point size so as to keep the focal point size after the change to be constant. In the case of executing the fine-tuning control, the main controller 152 may repeat control of detecting the focal point size after the change, comparing the detected focal point size with a set focal point size, and finely tuning in accordance with the set focal point size.

As described later, the change of the focal point size described in this embodiment aims to realize both a low possibility of a focal point burn in large size and a high resolution in imaging with the focal point of small size. Therefore, changing the focal point size to a set one and maintaining the focal point size leads to more demonstration of the characteristics of the respective focal point sizes. For example, high-resolution imaging is desired in a case that the focal point size is decreased, and it is impossible to accomplish the desire if the focal point size is increased by mistake. On the contrary, if the focal point size becomes smaller than a set value, the possibility of a focal point burn becomes higher. In this embodiment, it is expected to use for imaging for a longer hours by aiming to realize both the low possibility and the high resolution as described above, and it is not desired to decrease the focal point size more than necessary. Therefore, specifically in the case of decreasing the focal point size, a proper focal point size exists, and it becomes possible to balance both the high resolution and the long-hour imaging by keeping the proper focal point size.

The fine-tuning of the focal point size may be executed regardless of the size of the focal point, but may be executed only when the focal point size is small. In this case, at the time of change of the focal point size, the main controller 152 determines whether to increase or decrease the focal point size and, when decreasing the focal point size, actuates the aforementioned fine-tuning control. After that, in the case of increasing the focal point size, the main controller 152 ends the aforementioned fine-tuning control.

Although the change control and the fine-tuning control on the focal point size can be realized in parallel as described above, the functions thereof are definitely distinguished. The fine-tuning control aims to solve an inconvenience due to occurrence of a variation in focal point size by keeping the focal point size constant as described above. On the other hand, the change control of the focal point size aims to realize different functions depending on the focal point size by positively changing the focal point size. The focal point size before the fine-tuning and the focal point size after the fine-tuning are not used in parallel. Merely, one of the sizes is a focal point size to be set and the other is a focal point size not to be set. In the case of independently using the fine-tuning function, it is not supposed to use a plurality of focal point sizes. For changing a focal point size to use a plurality of focal point sizes, changing a filament has been performed in general, which is completely different from the fine-tuning control of a focal point size for the purpose of not changing a focal point size.

In the operation of the scan controller 131, the operations of the acquiring part 150, the determining part 151, and the main controller 152 have been separately described. In the following description, the operation of the main controller 152 alone will also be described as the operation of the scan controller 131.

An example of the operation of the X-ray CT apparatus 100 will be described, centering on the change of the size of the real focal point $F_{EB}$. Firstly, a real prep scan will be described as an example.

A real prep scan is a technique of determining a moment at which a contrast agent administered to the subject P flows into a slice of interest based on the CT value of an image obtained by a scan at low doses and shifting to a real scan when the CT value increases up to a certain point.

The scan controller 131 drives each unit of the X-ray CT apparatus under the imaging conditions for the prep scan, compares the CT value of the reconstructed image with a threshold and, when the CT value exceeds the threshold, drives each unit of the X-ray CT apparatus under the imaging conditions for the real scan.

For the X-ray tube 1, the following imaging conditions are required for the prep scan. The scan controller 131 superposes the same positive potential on the electric potentials of both the X electrodes 16a and 16b and the electrical potentials of both the Y electrodes 17a and 17b so that electrons emitted from the coil filament 15 of the X-ray tube 1 are radiated to the anode 22 with the real focal point $F_{EB}$ of small size.

Further, for the X-ray tube 1, the following imaging conditions are required for the real scan. The scan controller 131 superposes the same negative potential on the electric potentials of both the X electrodes 16a and 16b and the electric potentials of the Y electrodes 17a and 17b so that electrons emitted from the coil filament 15 of the X-ray tube 1 are radiated to the anode 22 with the real focal point $F_{EB}$ of large size.

Under the imaging conditions for the prep scan and the imaging conditions for the real scan, a whole imaging range of the subject P, the range of each of the sections divided within the whole imaging range, a helical pitch (HP), a rotation speed, a tube voltage (kV), a tube current (mA), and so on can be set by inputting. For this, these settings can be generated by causing the display device 137 to display a setup screen and inputting with the input device 138 while referring to the setup screen. These settings are outputted as control signals to each unit.

In the prep scan, the scan controller 131 follows the imaging conditions for the prep scan having been inputted. That is to say, by radiating an X-ray around a slice of interest at low doses and with the real focal point $F_{EB}$ of large size, the scan controller 131 controls to reconstruct an image at low resolution. Then, the scan controller 131 compares the CT value of the reconstructed image with a threshold and, when the CT value exceeds the threshold, shifts to the real scan. In the real scan, the scan controller 131 follows the imaging conditions for the real scan having been inputted. That is to say, by radiating an X-ray around a slice of interest at a predetermined dose with the real focal point $F_{EB}$ of small size, an image is reconstructed at predetermined resolution.

Figure 5:
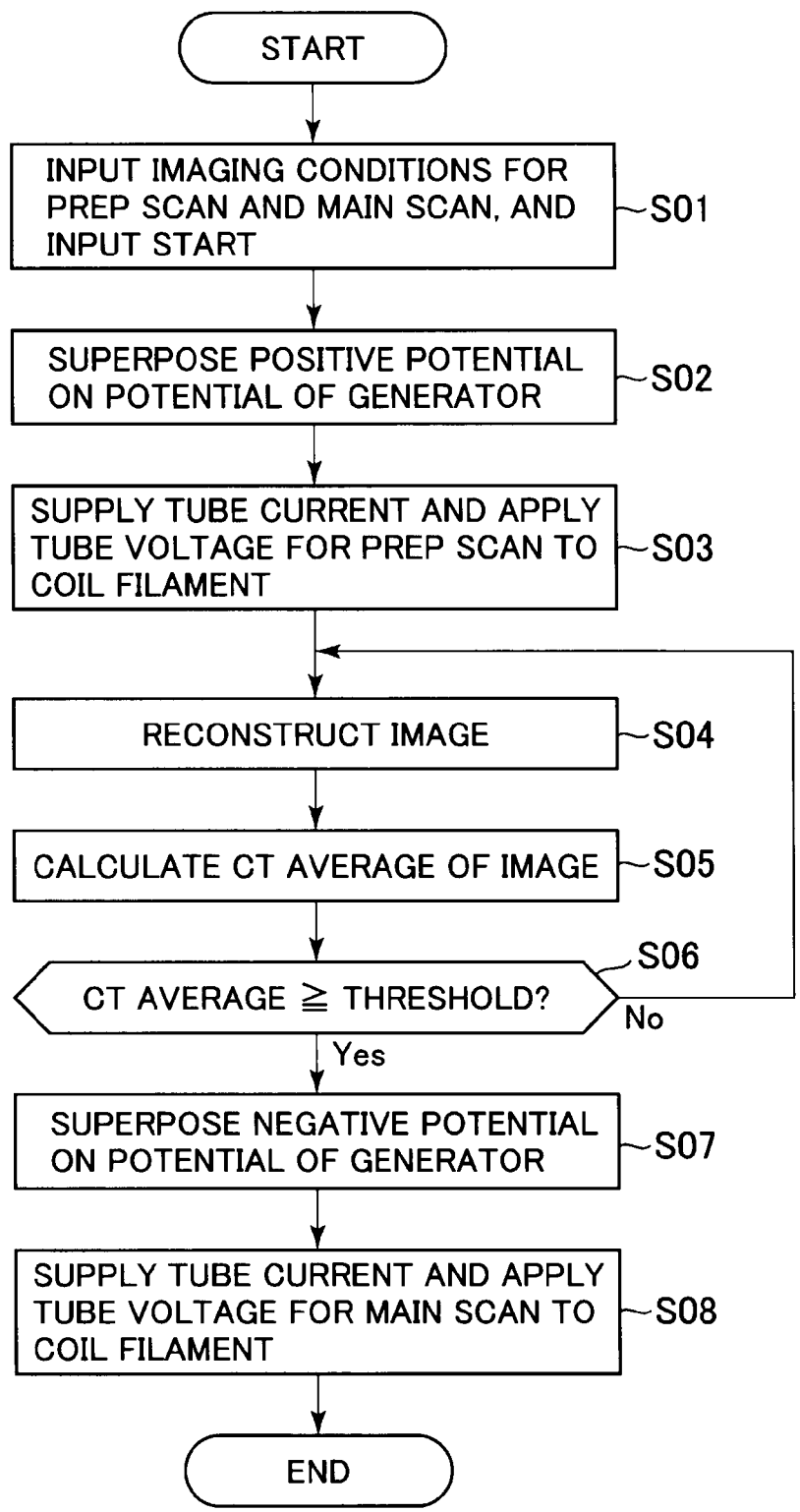
FIG. 5 is a flow chart showing an operation of a change control of the size of a real focal point in a real prep scan.

FIG. 5 is a flow chart showing an operation of the change control of the size of the real focal point $F_{EB}$ relating to the real prep scan.

Firstly, into the scan controller 131, the imaging conditions for the prep scan and the real scan are inputted, and thereafter, a signal of pressing down a start button is inputted (S01).

When the start button is pressed down, the scan controller 131 outputs a control signal to the high-voltage generating device 113, and superposes the same positive potential on the electric potentials of the X electrodes 16a and 16b and the Y electrodes 17a and 17b (S02). The scan controller 131 supplies a tube current and applies a tube voltage to the coil filament 15 in accordance with the imaging conditions for prep scan (S03).

While controlling the X-ray tube 1 in steps S02 and S03, the scan controller 131 moves the couch top 121 so as to locate the rotating gantry on an inputted slice of interest, and rotates the rotating gantry 111. That is to say, controlled by the scan controller 131, the X-ray CT apparatus 100 firstly executes a prep scan. Moreover, at this prep scan stage, due to the control by the scan controller 131, the beam diameter of the electron beam EB is increased. Consequently, the size of the real focal point $F_{EB}$ on the anode 22 is large-size.

Then, in parallel with the prep scan, the scan controller 131 controls the reconstruction processor 134 to reconstruct an image from projection data obtained by the prep scan (S04). When the image is reconstructed, the scan controller 131 reads out the reconstructed image from the image storage 135, extracts the CT values of a plurality of pixels within a region of interest ROI set in advance, and calculates an average CTave. of the CT values (S05). Then, the scan controller 131 compares a previously stored threshold TH with the CT average CTave. (S06).

In a case that the result of the comparison shows the CT average CTave. has not reach the threshold TH (S06, No), the scan controller 131 controls to continue the prep scan with the real focal point $F_{EB}$ of large size in steps S02 and S03, and controls to continue the comparison of the CT average CTave. with the threshold TH in steps S04 through S06.

On the other hand, in a case that the result of the comparison shows the CT average CTave. has reached the threshold TH (S06, Yes), the scan controller 131 shifts to control for the real scan.

That is to say, the scan controller 131 outputs a control signal to the high-voltage generating device 113 to superpose the same negative potential on the electric potentials of the X electrodes 16a and 16b and the Y electrodes 17a and 17b (S07). The scan controller 131 applies the tube voltage and tube current according to the real scan conditions via the coil filament 15 (S08).

The scan shifts to the real scan, and the process advances to step S07. Moreover, in accordance with shift to the real scan, the scan controller 131 decreases the beam diameter of the electron beam EB and the size of the real focal point $F_{EB}$ on the anode 22 is changed to the small size.

The real scan is continued until end conditions are satisfied. The end conditions can be conditions such as a scheduled duration, a scheduled number of rotations and, in the case of a helical scan, completion of data acquisition in a scheduled helical scan range. When the end conditions are satisfied, the real scan ends.

Figure 7A:
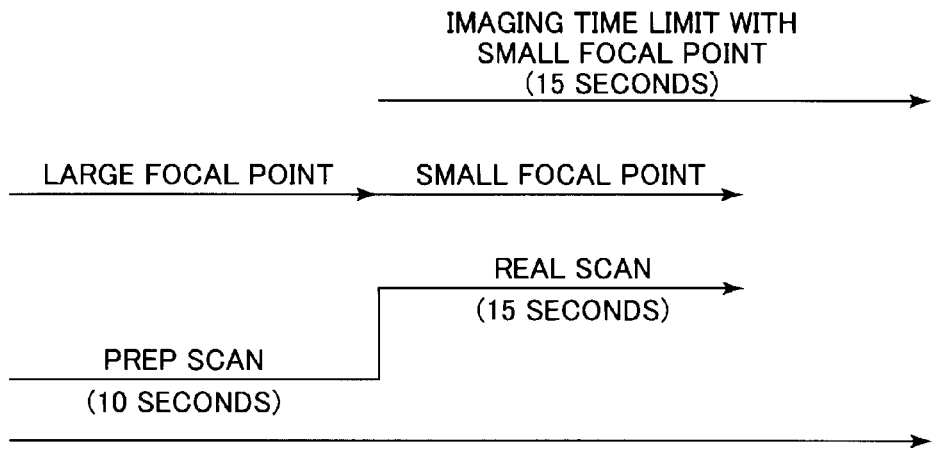
FIGS. 7A-7C are views showing a real prep scan in this embodiment and in a conventional technique.
Figure 7B:
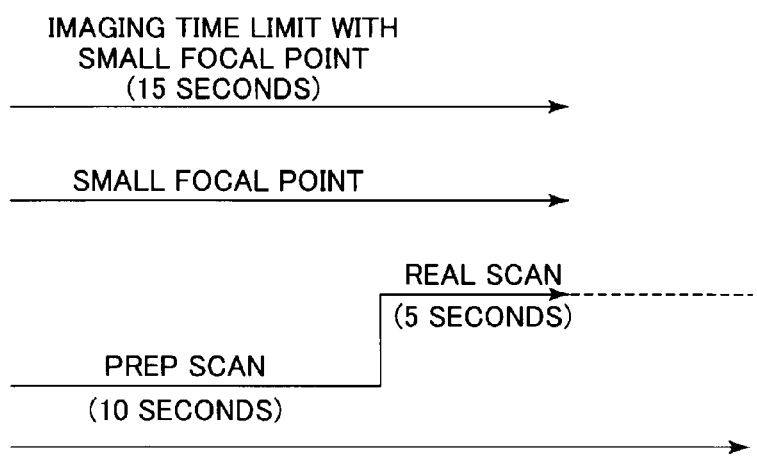
Figure 7C:
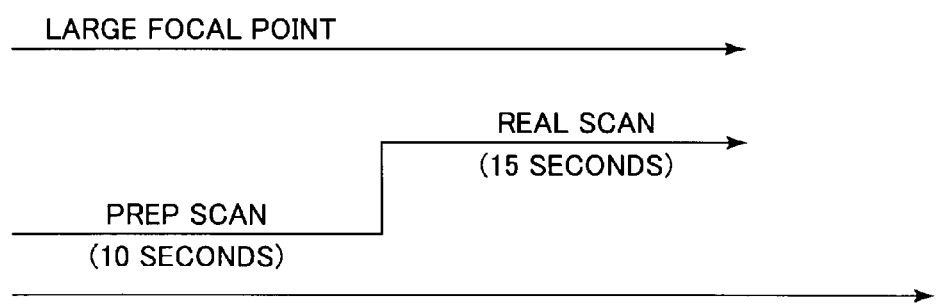

A relation between change of a scan aspect and change of the size of the real focal point $F_{EB}$ in the real prep scan of the X-ray CT apparatus will be described based on FIGS. 6 and 7A-7C. FIG. 6 is a schematic view showing change of a scan aspect based on the CT value and the size of the real focal point $F_{EB}$ during the scan. FIGS. 7A-7C are views showing the real prep scan in this embodiment and in a conventional technique.

Firstly as shown in FIG. 6, when the CT value CTave. is lower than the threshold TH, the scan controller 131 controls to execute a prep scan. The scan controller 131 increases the beam diameter of the electron beam EB emitted from the coil filament 15 and increases the size of the real focal point $F_{EB}$ on the anode 22. During this prep scan, the size of the real focal point $F_{EB}$ of the electrons focusing on the anode 22 is large, and therefore, the anode 22 is hard to cause a focal point burn.

As a contrast agent flows into a slice of interest, the CT value CTave. gradually increases. When the CT value CTave. exceeds the threshold TH, the scan controller 131 changes the scan conditions to those for the real scan. The scan controller 131 decreases the beam diameter of the electron beam EB radiated from the coil filament 15, and changes the size of the real focal point $F_{EB}$ on the anode 22 to the small size.

In the conventional techniques, as shown in FIGS. 7B and 7C, in the case of executing the real prep scan, it is impossible to quickly switch the size of the real focal point $F_{EB}$ during the scan. Therefore, from the start of the real prep scan to the end of the real scan, electrons are radiated with the real focal point $F_{EB}$ of fixed size to the anode 22 and an X-ray is generated. When the size of the real focal point $F_{EB}$ is fixed to a small size, there is a need to count down the remaining time before occurrence of a problem on the anode 22 due to a focal point burn, from the beginning of the real prep scan. Therefore, it is impossible to obtain a satisfactory imaging time in the real scan.

On the other hand, when the size of the real focal point $F_{EB}$ is fixed to a large size, the need for getting anxious about a focal point burn on the anode 22 is eliminated, but a reconstructed image becomes low-resolution.

On the other hand, as shown in FIG. 7A, in the X-ray CT apparatus 100 according to this embodiment, when the scan shifts to the real scan, the size of the real focal point $F_{EB}$ of electrons focusing on the anode 22 becomes small, and a focal point burn on the anode 22 becomes easy to occur. However, since the size has been large during the prep scan, it is possible to execute the real scan by using all of the remaining time before the anode 22 causes a trouble due to a focal point burn. That is to say, it is possible to extend an imaging time in the real scan and also obtain a reconstructed image of high resolution.

Next, a collective scan of a plurality of sites will be described as an example.

In the case of a collective scan of a plurality of sites, a plurality of successive sites are considered as one radiation range, and an imaging position is successively moved from the start to the end of the range. In this case, the scan conditions are previously set for each site and, when the imaging position reaches each site, the scan conditions are changed to the scan conditions for the site in real time.

A radiation range and a section representing each site are previously inputted by using the input device 138 with reference to a scanogram displayed on the display device 137. The scanogram is a two-dimensional transmission image of a subject captured prior to the real scan. Each pixel of the scanogram is associated with each imaging position.

For example, the radiation range is determined by displaying a rectangular figure on the scanogram and designating the range via the displayed figure. The scan controller 131 converts to imaging positions the coordinates of pixels in which both the short sides of the rectangular are drawn, and incorporates these imaging positions into control information as the start position and end position of radiation.

Further, sectioning into the plurality of sites can be determined by, for example, displaying a line that divides the rectangular figure and designating sections via the displayed line. The scan controller 131 converts to the imaging positions the coordinates of the pixels in which both sides of sections divided by the figure and the line of the rectangular indicating the radiation range are drawn, and incorporates the imaging positions into the control information as the start position and end position of each section. The figure and line of the rectangular can be changed with a mouse of the input device 138, for example.

The imaging conditions for a section representing each site are previously inputted by using the input device 138 with reference to a setup screen displayed on the display device 137, and incorporated into the control information by the scan controller 131.

The scan controller 131 instructs collective scanning of a plurality of sites in accordance with the thus set scan conditions. To be specific, the scan controller 131 rotates the gantry 111 and causes the X-ray tube 1 to radiate an X-ray, while moving the couch top from the start position to the end position of the radiation range. Moreover, the scan controller 131 monitors the position of the couch top 121 and, when the imaging position reaches the next section, controls each unit of the X-ray CT apparatus 100 so as to radiate and detect the X-ray under the imaging conditions inputted for the section and reconstruct an image.

The scan controller 131, when the imaging site shifts to a next section, changes the size of the real focal point $F_{EB}$ in accordance with the section. For example, in a case that the size of the real focal point $F_{EB}$ has been inputted for each site at the time of input of the imaging conditions, the size of the real focal point $F_{EB}$ is changed in accordance with the input. Moreover, in a case that a tube current has been inputted for each section at the time of input of the imaging conditions, the size of the real focal point $F_{EB}$ is changed in accordance with the tube current.

The relation between the tube current and the size of the real focal point $F_{EB}$ is previously stored by step function or the like. For example, the size of the real focal point $F_{EB}$ is large when the tube current is a large current within a predetermined range, and the size of the real focal point $F_{EB}$ is small when the tube current is a small current within a predetermined range. The range of a large current and the range of a small current can be defined as a range of available tube current depending on the size of the real focal point $F_{EB}$ of electrons.

FIG. 8 is a flow chart showing an operation of the change control of the size of the real focal point $F_{EB}$ in the case of collectively scanning a plurality of sites. Firstly, into the scan controller 131, sections of the radiation range and the imaging conditions for each section are inputted, and then, a signal to press the start button is inputted (S11).

After the start button is pressed down, in a case that the tube current for a section to be irradiated with an X-ray is a large current (S12, Yes), the scan controller 131 superposes the same positive potential on the potentials of the X electrodes 16a and 16b and the Y electrodes 17a and 17b (S13). On the other hand, in a case that the tube current for a section to be irradiated with an X-ray is a small current (S12, No), the scan controller 131 superposes the same negative potential on the electric potentials of the X electrodes 16a and 16b and the Y electrodes 17a and 17b (S14).

Then, the scan controller 131 outputs a control signal to the high-voltage generating device 113, and applies a tube voltage and tube current of the imaging conditions for the final section to the coil filament 15 (S15). Prior to control on the X-ray tube 1 at S15, the scan controller 131 positions the gantry 111 to the start position of a first section. In parallel with the control on the X-ray tube 1, the scan controller 131 rotates the gantry 111 and moves the couch top 121.

When the imaging position reaches a next section (S16, YES), the scan controller 131 executes the following control. That is to say, in a case that the tube current for a section to be irradiated with an X-ray is a large current (S17, Yes), the scan controller 131 superposes the same positive potential on the electric potentials of the X electrodes 16a and 16b and the Y electrodes 17a and 17b (S18). On the other hand, in a case that the tube current for a next section is a small current (S17, No), the scan controller 131 superposes the same negative potential on the electric potentials of the X electrodes 16a and 16b and the Y electrodes 17a and 17b (S19).

Then, the scan controller 131 outputs a control signal to the high-voltage generating device 113 to apply a tube voltage and tube current of the imaging conditions for a next section to the coil filament 15 (S20).

This real scan is continuously executed until scans on all of the scheduled sections are finished. The real scan ends when scans on all of the sections are finished.

A relation between change of a scan aspect in a collective scan of a plurality of sites and change of the size of the real focal point $F_{EB}$ in the X-ray CT apparatus 100 will be described based on FIG. 9. FIG. 9 is a schematic view showing change of the size of the real focal point $F_{EB}$ associated with change of an imaging site.

When a next site is to be imaged and the tube current set for the next site is small, the scan controller 131 decreases the beam diameter of the electron beam EB emitted from the coil filament 15 and decreases the size of the real focal point $F_{EB}$ on the anode 22. On the other hand, when the next site is to be imaged and the tube current set for the next site is large, the scan controller 131 increases the beam diameter of the electron beam EB emitted from the coil filament 15 and increases the size of the real focal point $F_{EB}$ on the anode 22.

Conventionally, techniques of varying a tube current for each site in the case of collectively scanning a plurality of sites have been proposed. In the case of radiating an X-ray by using a coil filament of small size, there is essentially the upper limit of the tube current.

Therefore, in a case that a set tube current is more than the upper limit for the filament of small size, a change to a filament of large size is possible. Alternatively, it is also possible to use a coil filament of large size from the beginning to radiate an X-ray.

In the former case, when an imaged position reaches a section for which a tube current more than the upper limit for the small filament has been set, a tube current accurately reflecting the setting cannot be supplied and the quality of an image is thereby deteriorated.

Moreover, a change to a large filament is required. It takes a few seconds or more to change the filament, and the movement of the couch top 121 may be stopped.

In the latter case, it is possible to quickly finish a scan without stopping the movement of the couch top 121. However, the resolution of an image is low and it may be impossible to obtain a desired image quality.

On the other hand, the X-ray CT apparatus 100 according to this embodiment can accurately flow a set tube current through the coil filament 15. Therefore, it is expected to reconstruct a low-noise or high-resolution image in response to a desired tube current for each site, and it is also possible to speedily execute a collective scan of a plurality of sites without stopping the movement of the couch top.

Next, an ECG-gated scan will be described as an example.

Figure 10:
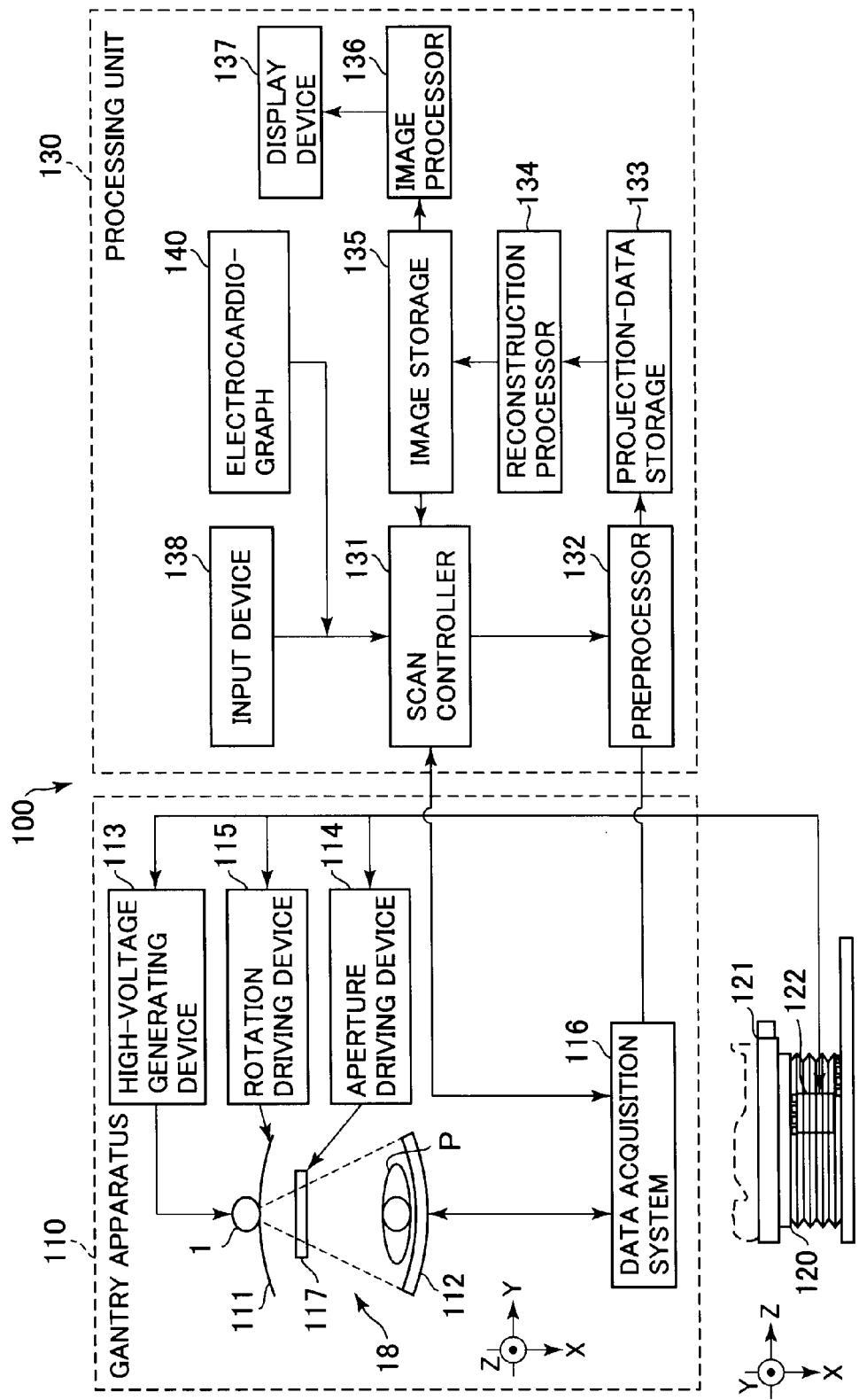
FIG. 10 is a block diagram showing an X-ray CT apparatus relating to an ECG-gated scan.

FIG. 10 is a block diagram showing the X-ray CT apparatus 100 relating to an ECG-gated scan. As shown in FIG. 10, the X-ray CT apparatus 100 includes an electrocardiograph 140. The electrocardiograph 140 detects electrocardiographic waveforms showing heart beats of a subject and outputs electrocardiographic waveform data to the processing unit 130. This electrocardiograph 140 has electrodes. The electrodes are attached to the chest and extremities of a subject P laid on the couch top 121. The electrocardiograph 140 continuously detects electrocardiographic waveform signals based on change in current value, change in voltage value, change in impedance, and so on caused between the electrodes, and executes AD conversion, thereby generating electrocardiographic waveform data in which electrocardiographic waveforms line up in the chronological order.

The scan controller 131 changes the size of the real focal point $F_{EB}$ of electrons emitted by the coil filament 15 between cases that a predetermined cardiac phase such as a P-wave appears and the other cases. For example, the scan controller 131 switches the real focal point $F_{EB}$ of electrons to the small size and increases the resolution in a case that electrocardiographic waveforms of identical cardiac phases appear, whereas switches the real focal point $F_{EB}$ of electrons to the large size in the other cases.

Alternatively, when variation of electrocardiographic waveforms is small, that is, when the heart is still (in diastasis), the scan controller 131 switches the real focal point $F_{EB}$ of electrons to the small size to increase the resolution, and switches the real focal point $F_{EB}$ of electrons to the large size in the other cases (that is, when the heart is sufficiently beats and the electrocardiographic waveform is largely moving). By switching the real focal point $F_{EB}$ to the small size at the moment to increase the resolution, it is possible to grasp a moment that the movement of the heart is small and execute imaging.

The moment when the movement of the heart is small is a time when blur is hard to occur or will not occur. This has not been realistic conventionally because it has been required to image the subject while the size of the focal point is kept small and a focal point burn has occurred. However, since the subject can imaged with increased resolution during small movement of the heart, imaging the subject with high resolution is enabled while continuing a scan for comparatively long hours.

Further, the reconstruction processor 134 extracts projection data obtained in X-ray radiation when a predetermined cardiac phase appears, and reconstructs an image.

Figure 11:
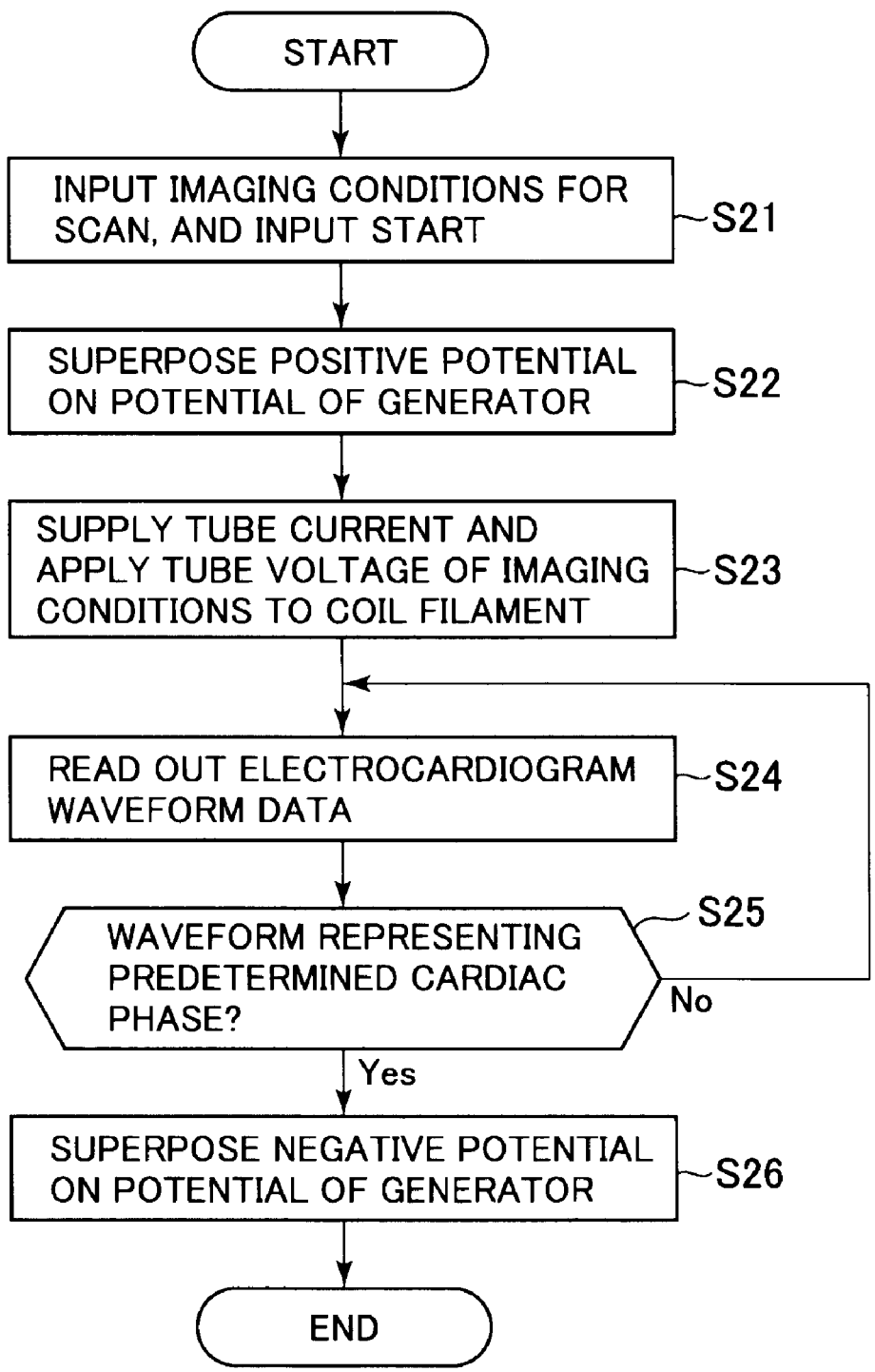
FIG. 11 is a flow chart showing a control operation of the size of a real focal point in the ECG-gated scan.

FIG. 11 is a flow chart showing a control operation of the size of the real focal point $F_{EB}$ relating to the ECG-gated scan. Firstly, into the scan controller 131, scan conditions are inputted and thereafter a signal of pressing down a start button is inputted (S21).

When the start button is pressed down, the scan controller 131 outputs a control signal to the high-voltage generating device 113 to superpose the same positive potential on the electric potentials of the X electrodes 16a and 16b and the Y electrodes 17a and 17b (S22). The scan controller 131 performs supply of a tube current and application of a tube voltage to the coil filament 15 under the imaging conditions for the prep scan (S23).

The scan controller 131 reads out electrocardiographic waveform data outputted from the electrocardiograph 140 at predetermined intervals (S24) and determines whether the data is that of a waveform representing a predetermined cardiac phase (S25). In a case that the electrocardiographic waveform data is not that of the predetermined cardiac phase (S25, No), the scan controller 131 repeatedly performs the determination in step S25 while continuing the scan. For example, for detecting an R-wave, the scan controller 131 determines a waveform based on whether an electric potential indicated by an electrocardiographic waveform exceeds a predetermined threshold.

On the other hand, in a case that the electrocardiographic waveform data is that of a waveform representing the predetermined cardiac phase (S25, Yes), the scan controller 131 superposes a negative potential (S26). This negative electric potential is such an electric potential that is negative with respect to the electric potential of the Wehnelt electrode 14, and the same electric potential is superposed on the electric potentials of the X electrodes 16a and 16b and the Y electrodes 17a and 17b.

A scan is continued until ending conditions such as a scheduled duration, a scheduled number of rotations and, in the case of a helical scan, completion of data acquisition within a scheduled helical scan range are satisfied. The scan ends when the conditions are satisfied.

Figure 12:
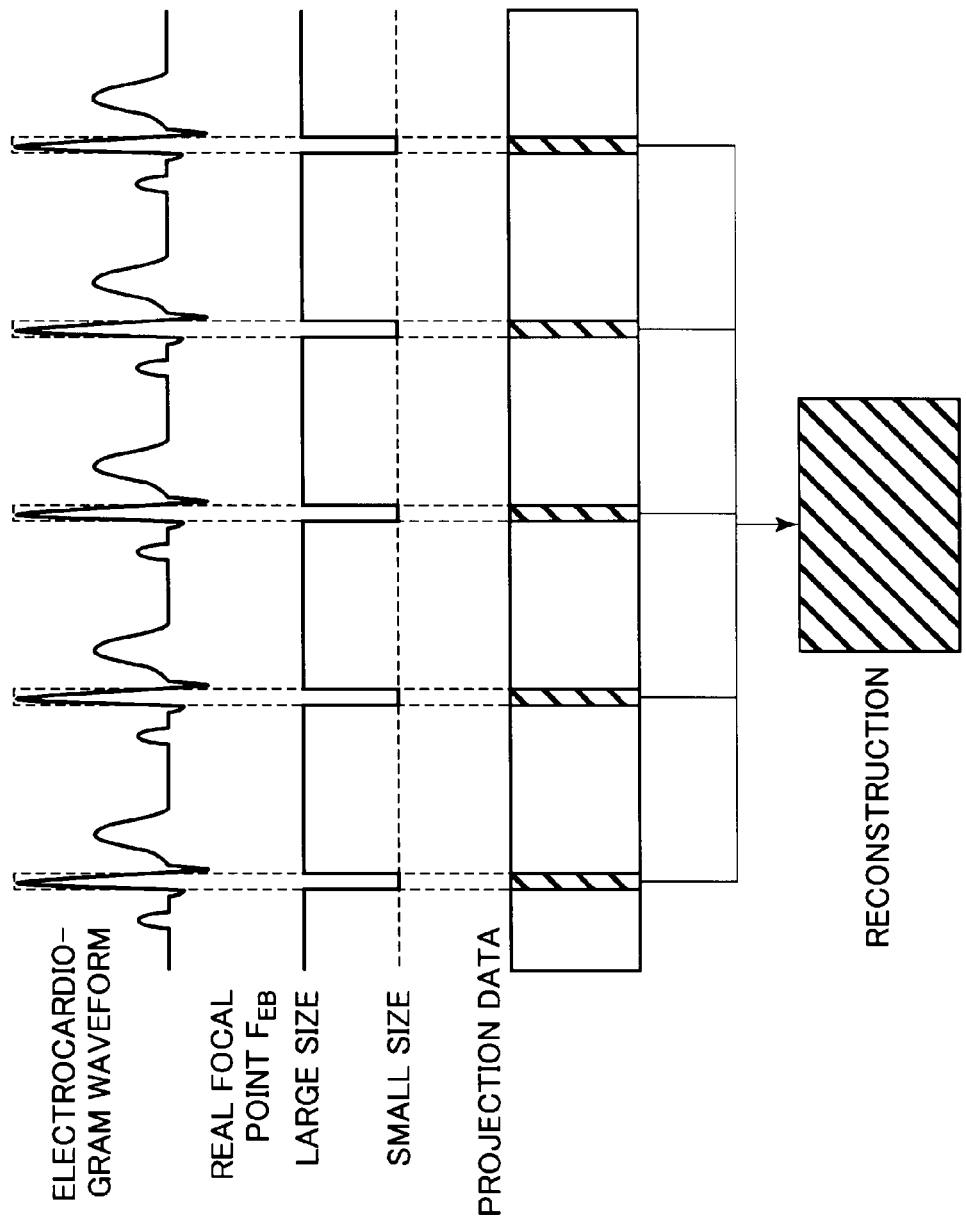
FIG. 12 is a schematic view showing change of the size of a real focal point in the ECG-gated scan.

Change of the size of the real focal point $F_{EB}$ relating to the ECG-gated scan of the X-ray CT apparatus 100 will be describe based on FIG. 12. FIG. 12 is a schematic view showing change of the size of the real focal point $F_{EB}$ relating to the ECG-gated scan.

For example, when an electrocardiographic waveform outputted from the electrocardiograph 140 is other than an R-wave, the scan controller 131 keeps the beam diameter of the electron beam EB emitted from the coil filament 15 large and keeps the size of the real focal point $F_{EB}$ on the anode 22 large. On the other hand, when an electrocardiographic waveform outputted from the electrocardiograph 140 indicates an R-wave, while this R-wave electrocardiographic waveform is being inputted, the scan controller 131 keeps the beam diameter of the electron beam EB emitted from the coil filament 15 small and keeps the size of the real focal point $F_{EB}$ on the anode 22 small.

Conventionally, techniques of extracting projection data of identical cardiac phases in synchronization with electrocardiographic waveforms and reconstructing an image have been proposed. However, in order to acquire enough projection data of identical cardiac phases for reconstruction, it is required to continue a scan for long hours to some extent. Then, in order to avoid trouble due to a focal point burn on the anode 22, there has been a need to make the real focal point $F_{EB}$ large-size. Therefore, it has been hard to realize both no trouble and a high-resolution image.

On the other hand, according to this embodiment, it is possible to make a reconstruction image of a desired cardiac phase high-resolution, and it is also possible to continue a scan without getting anxious about trouble due to a focal point burn on the anode 22.

Next, an example of changing the real focal point $F_{EB}$ for each view to reconstruct a high-resolution image, a low-noise image and an intermediate image at one time will be described.

The X-ray CT apparatus 100 changes the size of the real focal point $F_{EB}$ of electrons for each view. Then, the apparatus gathers projection data obtained by X-ray radiation, which are generated by radiation to the anode 22 with the real focal points $F_{EB}$ of identical sizes, respectively, and reconstructs images individually. Thus, the apparatus generates an image corresponding to the real focal point $F_{EB}$ of large size and an image corresponding to the real focal point $F_{EB}$ of small size, and also reconstructs an image based on all of the projection data. That is to say, by varying the size of the real focal point $F_{EB}$ of electrons for each view, the apparatus acquires a high-resolution image, a low-noise image and an intermediate image in the same slice of interest in one scan.

For capturing various types of images, conventional X-ray CT apparatuses need to execute scans for each type of image. However, the X-ray CT apparatus 100 is capable of reconstructing a high-resolution image, a low-noise image and an intermediate image in one scan.

In this embodiment, the scan controller 131 changes the electric potentials of the X electrodes 16a and 16b and the Y electrodes 17a and 17b for each X-ray radiation of the X-ray tube 1 while the gantry 111 is rotating.

Figure 13:
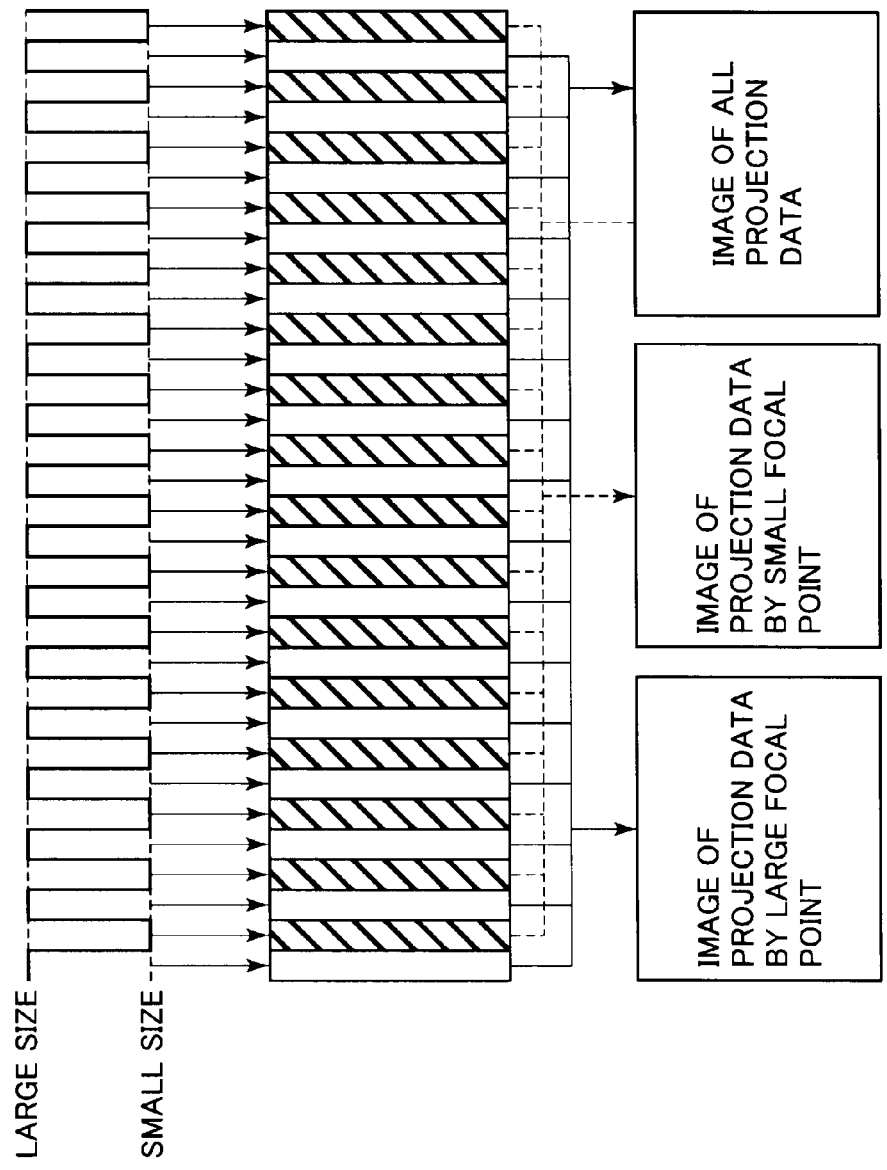
FIG. 13 is a schematic view showing change of the size of a real focal point and generation of an image for each view in the X-ray CT apparatus.

FIG. 13 is a schematic view showing change of the size of the real focal point $F_{EB}$ for each view and generation of images in the X-ray CT apparatus 100.

For example, in X-ray radiation for even numbers of times, the scan controller 131 superposes the same positive potential on the electric potentials of the X electrodes 16a and 16b and the Y electrodes 17a and 17b, thereby making the real focal point $F_{EB}$ of electrons large-size. In X-ray radiation for odd numbers of times, the scan controller 131 superposes the same negative potential on the electric potentials of the X electrodes 16a and 16b and the Y electrodes 17a and 17b, thereby making the real focal point $F_{EB}$ of electrons small-size.

That is to say, the scan controller 131 alternately switches the real focal point $F_{EB}$ between large-size and small-size every time the view switches. Each view may be associated with the size of the real focal point $F_{EB}$ and, when an X-ray is radiated in a certain view, the scan controller 131 may switch the size of the real focal point $F_{EB}$ to the size associated with the view.

Further, the reconstruction processor 134 extracts projection data generated by radiation of electrons with the real focal point $F_{EB}$ of small size and projection data generated by radiation of electrons with the real focal point $F_{EB}$ of large size and executes back projection of the respective data to reconstruct images. Moreover, the reconstruction processor 134 reconstructs an image from all of the projection data. To the projection data inputted into the reconstruction processor 134, a view number is attached. The reconstruction processor 134 determines the size of the real focal point $F_{EB}$ with reference to the view number.

For example, in a case that the real focal point $F_{EB}$ is alternately switched between large-size and small-size every time the view switches, the reconstruction processor 134 extracts projection data whose view numbers are even numbers and projection data whose view numbers are odd numbers, respectively, and generates respective images.

Figure 14:
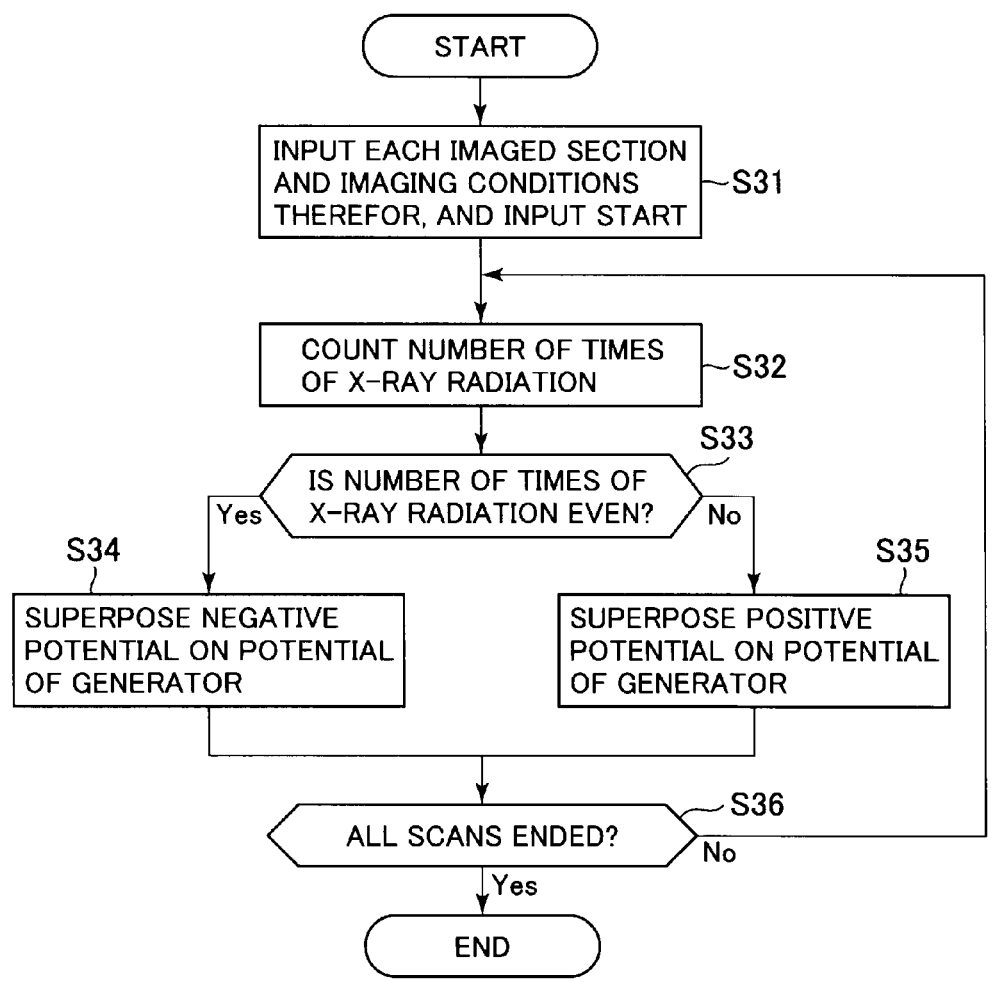
FIG. 14 is a flow chart showing an operation of control of switching the size of a real focal point of electrons for each view.

FIG. 14 is a flow chart showing a control operation of switching the size of the real focal point $F_{EB}$ of electrons for each view. In this operation, a case of alternately switching the real focal point $F_{EB}$ between large-size and small-size every time the view switches will be described.

To be specific, when the high-voltage generating device 113 supplies a high-voltage pulse current to the coil filament 15 (S31), the scan controller 131 counts the number of times of X-ray radiations (S32).

When the number of times of X-ray radiations is an even number (S33, Yes), for the next supply of a pulse current, the scan controller 131 superposes the same electric potential negative with respect to the electric potential of the Wehnelt electrode 14 on the electric potentials of the X electrodes 16a and 16b and the Y electrodes 17a and 17b (S34).

On the other hand, when the number of times of X-ray radiations is an odd number (S33, No), for the next supply of a pulse current, the scan controller 131 superposes the same electric potential positive with respect to the electric potential of the Wehnelt electrode 14 on the electric potentials of the X electrodes 16a and 16b and the Y electrodes 17a and 17b (S34).

When scheduled scans have not ended (S36, No), this real scan returns to step S32. The real scan ends when all the scans end.

Figure 15:
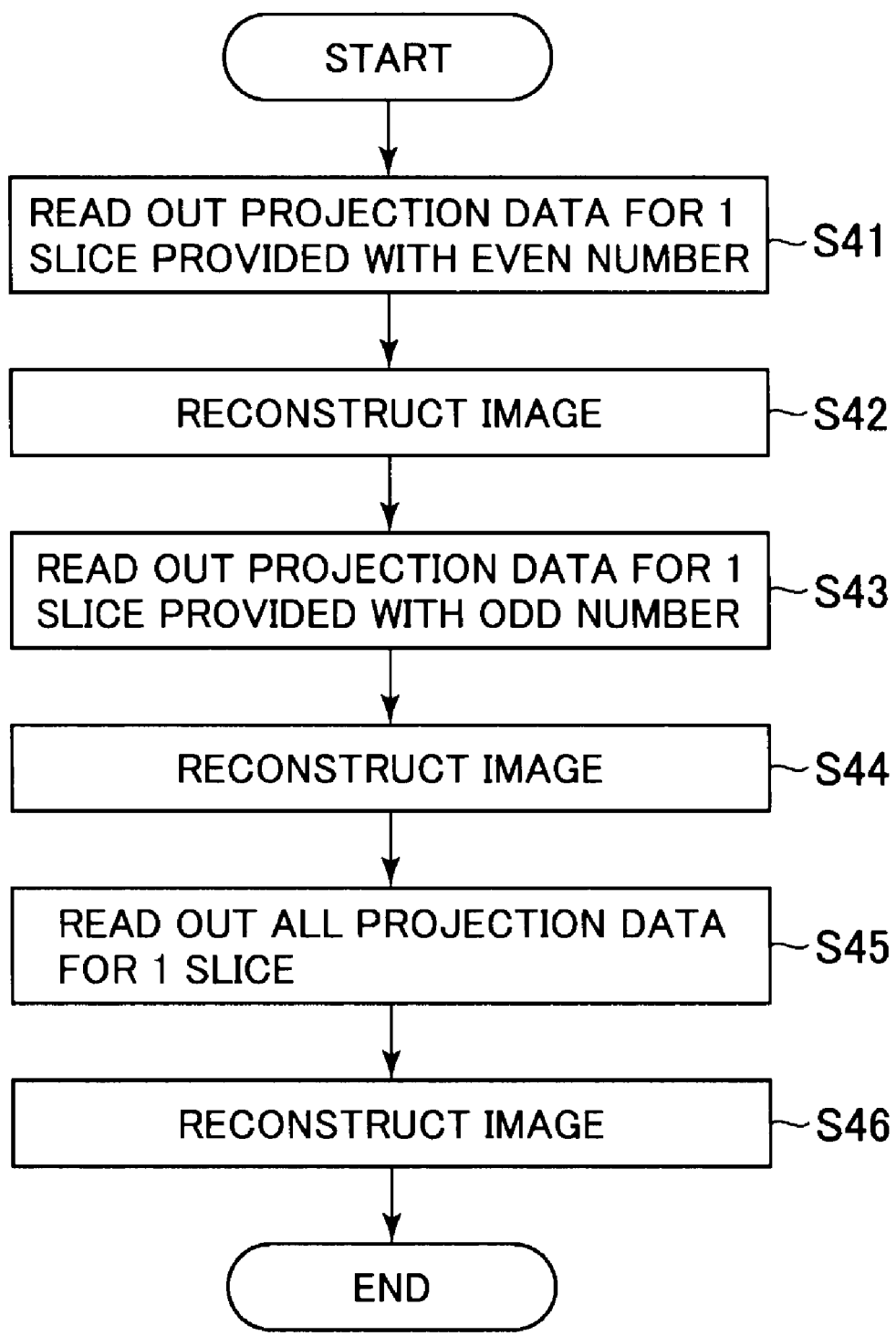
FIG. 15 is a flow chart showing a process of reconstructing an image.

FIG. 15 is a flow chart showing an image reconstruction process.

The reconstruction processor 134 reads out projection data for one slice provided with even view numbers from the projection data storage 133 (S41) and executes back projection of the projection data having been read out to reconstruct an image (S42). Next, the reconstruction processor 134 reads out projection data for one slice provided with odd view numbers from the projection data storage 133 (S43) and executes back projection of the projection data having been read out to reconstruct an image (S44). Furthermore, the reconstruction processor 134 reads out all of the projection data for one slice from the projection data storage 133 (S45) and executes back projection of the projection data having been read out to reconstruct an image (S46).

The above embodiment described switching processes between the large focal point and the small focal point during scanning, while the size of the focal points to be switched (i.e. the large focal point and the small focal point) may be variable. Particularly, if the size of the small focal point is appropriately determined, such determination is available for the purpose of avoiding the focal point burn intended by this embodiment. Thus, determination of the size of the focal point during scanning is described as follows.

The size of the small focal point may be entered manually. For example, the size of the small focal point is entered from the input devices 138 shown in FIG. 4, and the entered value is determined as the size of the small focal point. Alternatively, a plurality of sizes of the focal point is stored in advance, one of which may be selected for the small size. Further, the position and the timing for switching the size of focal point are also entered as predetermination. Then, when the size of the focal point is switched from a large size to a small size, the size of the focal point is changed to the predetermined small size at the timing of the predetermined timing. The size of the focal point is variably predetermined according to the value of the tube current.

The above may be applied to the example shown in FIG. 6. A threshold is entered from the input device 138, and the scan controller 131 changes the size of the focal point to the small size when CT value exceeds the threshold. When applied to the example of FIG. 9, a section requiring a high resolution imaging (e.g. chest section) is predetermined from the input device 138, and the scan controller 131 changes the size of the focal point to the small size when imaging the subject in this section. When applied to the example of FIG. 12, a waveform indicating ceratin cardiac phase is predetermined from the input device 138, and the scan controller 131 changes the size of the focus point to the small size at the timing of this waveform appearance.

When applied to the example of FIG. 13, a view number setting is entered from the input device 138, and the scan controller 131 changes the size of the focus point to the small size according to the view number setting.

Further, the scan controller 131 may determine the small size from the relation of the radiation time and thermal duration, to change the size of the focus point to this the determined size. For example, the scan controller 131 sets the relation of the radiation time and thermal duration as proportional. Specifically, it is supposed that a predicted radiation time is 2 t and the corresponding size of the focus point is 2S.

In this case, when the radiation time is expected longer, to be 4 t, the size of the focal point is set to be 4 S. Thus, the large size 4 S of the focal point reduces the risk of focal point burn against long radiation time 4 t. On the contrary, when the radiation time is expected shorter, to be t, the size of the focus point is set to be S. Thus, the small size S of the focal point allows high resolution imaging while short radiation time prevents a focal point burn.

As described above, the X-ray CT apparatus 100 is equipped with the X-ray tube 1 having the X electrodes 16a and 16b and the Y electrodes 17a and 17b, which are the generators that generate an electric field on the radiation path L of electrons to focus the electrons in accordance with the output. The scan controller 131 is configured to control the output of the generators and change the size of the real focal point $F_{EB}$ of the electrons during a scan by the control.

As an example, the scan controller 131 measures the CT value of an image, switches from the prep scan to the real scan based on the CT value, and changes the size of the real focal point $F_{EB}$. When changing the size, for example, the scan controller 131 changes the size of the real focal point $F_{EB}$ from a large size to a small size.

This enables execution of the real scan by using the whole remaining time before trouble occurs due to a focal point burn on the anode 22. Therefore, the quality of an image increases.

Figure 16:
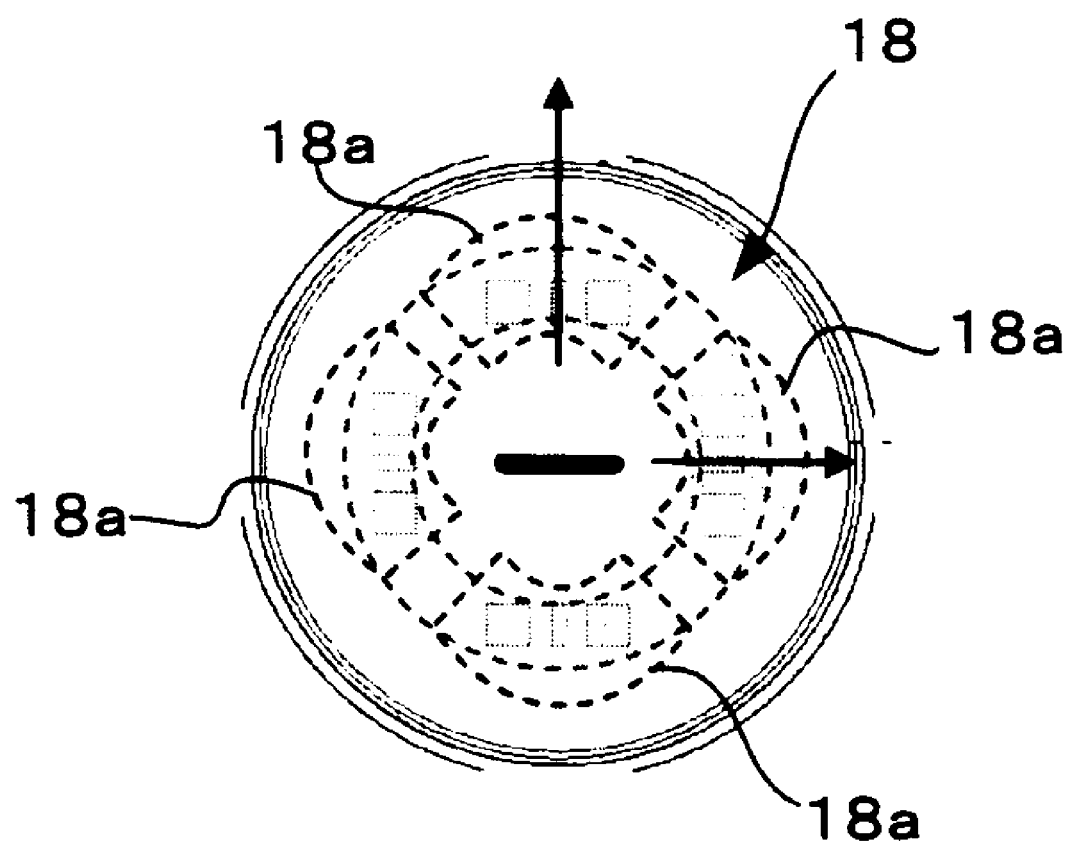
FIG. 16 is a schematic cross-sectional view of the X-ray tube cut orthogonally to the electron emission direction.

Although an electrode pair generating an electric field is used as the generators in this embodiment, an electromagnetic deflector 18 may be arranged outside the vacuum shield chamber 21 as shown in FIG. 16.

This electromagnetic deflector 18 is arranged so that the central axis of a toroidal coil 18a disposed so as to surround the path L coincides with the path L. This electromagnetic deflector 18 generates a large electromagnetic field and makes it possible to control the electron beam EB via the magnetic field.

Further, for example, as an imaging position controller, the scan controller 131 continuously changes an X-ray radiation position within a radiation range having been inputted, and the scan controller 131 also changes the size of the real focal point $F_{EB}$ for each section that the radiation position reaches. For example, in a case that the setting of a tube current is inputted for each section, the scan controller 131 changes the size of the real focal point $F_{EB}$ in accordance with a tube current set for a section that the X-ray radiation position reaches, and then changes the tube current to the set one.

Thus, it is possible to pass the set tube current through the coil filament 15 with accuracy. Consequently, it is possible to speedily execute a collective scan of a plurality of sites without stopping the movement of the couch top 121. Also, it can be expected to reconstruct a low-noise or high-resolution image for each site in accordance with a desired tube current.

Further, as one example, the X-ray CT apparatus 100 is connected to the electrocardiograph 140 configured to acquire electrocardiographic waveforms of a subject so as to be capable of data communication, and the scan controller 131 changes the size of the real focal point $F_{EB}$ in synchronization with appearance of a predetermined waveform outputted from the electrocardiograph. For example, the scan controller 131 changes the size of the real focal point $F_{EB}$ to large-size in synchronization with appearance of a waveform other than a predetermined waveform such as an R-wave, and changes the size of the real focal point $F_{EB}$ to small-size in synchronization with appearance of the predetermined waveform such as an R-wave.

Thus, it is possible to make a reconstruction image at a desired cardiac phase high-resolution, whereas it is possible to continue a scan without getting anxious about trouble due to a focal point burn on the anode 22.

Further, as one example, the scan controller 131 changes the size of the real focal point $F_{EB}$ for each view that the X-ray tube 1 radiates an X-ray. For example, the scan controller 131 alternately changes between the real focal point $F_{EB}$ of large size and the real focal point $F_{EB}$ of small size every time the view varies. Then, the reconstruction processor 134 generates a first image based on projection data obtained by detecting the X-ray radiated in views of the real focal point $F_{EB}$ of large size, generates a second image based on projection data obtained by detecting the X-ray radiated in views of the real focal point $F_{EB}$ of small size, and generates a third image based on projection data obtained by detecting the X-ray radiated in views of the large and small focal point sizes. The reconstruction processor 134 may be configured to, when selection of any of the first to third images is inputted by using the input device 138, selectively generate only the selected image.

Thus, it is possible to acquire a high-resolution image, a low-noise image and an intermediate image in one slice of interest in one scan.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus configured to reconstruct an image from projection data obtained in a scan by radiation and detection of an X-ray, the X-ray CT apparatus comprising:
a setting part configured to set an imaging condition for a real scan or a prep scan, which is scanning by a resolution lower than the real scan;
an X-ray tube having a filament, an anode, and generators arranged opposite to each other across a path heading from the filament to the anode and configured to output an electric field or a magnetic field onto the path to focus an electron beam heading from the filament to the anode in accordance with the output under the imaging condition set by the setting part, the X-ray tube being configured to radiate the X-ray;
a detector configured to detect the X-ray radiated from the X-ray tube;
a reconstructing part configured to reconstruct an image from the projection data based on the detection by the detector;
an acquiring part configured to determine a CT value from the image reconstructed by the reconstructing part;
a determining part configured to determine whether the CT value is included within a reference range; and
a controller configured to control an intensity of the output of the generators with reference to a result of the determination by the determining part to change a focal point size of the electron beam to a different size depending on the imaging condition during the scan, while continuously switching the scan between the prep scan and the real scan and changing the focal point size.

2. The X-ray CT apparatus according to claim 1, wherein the controller is configured to, when the CT value exceeds a threshold, switch the scan from the prep scan to the real scan and to change the focal point size from a large size to a small size.

3. The X-ray CT apparatus according to claim 2, wherein the controller is configured to increase a tube current of the X-ray tube when changing the focal point size from the large to the small size.

4. The X-ray CT apparatus of claim 1, wherein the controller is configured to change the focal point size from a large size to a small size when the CT value is included within the reference range and change the focal point size from a small size to a large size when the CT value is out of the reference range.

5. An X-ray CT apparatus configured to reconstruct an image from projection data obtained in a scan by radiation and detection of an X-ray, the X-ray CT apparatus comprising:
an X-ray tube having a filament, an anode, and generators arranged opposite to each other across a path heading from the filament to the anode and configured to output an electric field or a magnetic field onto the path to focus an electron beam heading from the filament to the anode in accordance with the output, the X-ray tube being configured to radiate the X-ray;
a detector configured to detect the X-ray radiated from the X-ray tube;
a reconstructing part configured to reconstruct an image from the projection data based on the detection by the detector;
an acquiring part configured to acquire a parameter indicating a status of the scan, which is a value indicating a radiation position of the X-ray to a subject;
a determining part configured to determine whether the parameter acquired by the acquiring part during the scan is included within a reference range that is a positional section in a radiation range of the X-ray into sections; and
a controller configured to control an intensity of the output of the generators with reference to a result of the determination by the determining part to change a focal point size of the electron beam to a different size depending on the determination result during the scan, while continuously changing the radiation position of the X-ray within the radiation range and changing the focal point size for each of the sections that the radiation position of the X-ray reaches.

6. The X-ray CT apparatus according to claim 5, further comprising a manipulation part configured to input a setting of the positional section.

7. The X-ray CT apparatus according to claim 6, wherein:
the manipulation part is configured to input, in addition to the positional section, a set value of a tube current for each of the sections; and
the controller is configured to change the focal point size in accordance with the tube current for the section that the radiation position of the X-ray reaches and then to change the tube current.

8. The X-ray CT apparatus of claim 5, wherein the controller is configured to change the focal point size from a large size to a small size when the parameter is included within the reference range and change the focal point size from a small size to a large size when the parameter is out of the reference range.

9. An X-ray CT apparatus connected to an electrocardiograph configured to acquire an electrocardiographic waveform of a subject so as to be capable of data communication, the X-ray CT apparatus configured to reconstruct an image from projection data obtained in a scan by radiation and detection of an X-ray, the X-ray CT apparatus comprising:
an X-ray tube having a filament, an anode, and generators arranged opposite to each other across a path heading from the filament to the anode and configured to output an electric field or a magnetic field onto the path to focus an electron beam heading from the filament to the anode in accordance with the output, the X-ray tube being configured to radiate the X-ray;
a detector configured to detect the X-ray radiated from the X-ray tube;
a reconstructing part configured to reconstruct an image from the projection data based on the detection by the detector;
an acquiring part configured to acquire the electrocardiographic waveform from the electrocardiograph;
a determining part configured to determine whether the electrocardiographic waveform acquired by the acquiring part during the scan is a specific waveform indicating a specific cardiac phase; and
a controller configured to control an intensity of the output of the generators with reference to a result of the determination by the determining part to change a focal point size of the electron beam to a different size depending on the determination result during the scan, in synchronization with an appearance of the specific waveform from a waveform outputted from the electrocardiograph.

10. The X-ray CT apparatus according to claim 9, wherein the controller is configured to change the focal point size from a large size to a small size in synchronization with an appearance of a waveform indicating diastasis.

11. The X-ray CT apparatus according to claim 9, wherein the controller is configured to change the focal point size from a small size to a large size in synchronization with an appearance of a waveform indicating cardiac motion.

12. The X-ray CT apparatus of claim 9, wherein the controller is configured to change the focal point size from a large size to a small size when the electrocardiographic waveform is the specific waveform and change the focal point size from a small size to a large size when the electrocardiographic waveform is not the specific waveform.

13. An X-ray CT apparatus configured to reconstruct an image from projection data obtained in a scan by radiation and detection of an X-ray, the X-ray CT apparatus comprising:
an X-ray tube having a filament, an anode, and generators arranged opposite to each other across a path heading from the filament to the anode and configured to output an electric field or a magnetic field onto the path to focus an electron beam heading from the filament to the anode in accordance with the output, the X-ray tube being configured to radiate the X-ray;
a detector configured to detect the X-ray radiated from the X-ray tube;
a reconstructing part configured to reconstruct an image from the projection data based on the detection by the detector;
an acquiring part configured to acquire a parameter indicating a view number of the X-ray radiation;
a determining part configured to determine whether the parameter acquired by the acquiring part during the scan is included within a reference range; and
a controller configured to control an intensity of the output of the generators with reference to a result of the determination by the determining part to change a focal point size of the electron beam to a different size for every view number during the scan.

14. The X-ray CT apparatus according to claim 13, wherein the controller is configured to alternately change between the focal point size of large size and the focal point size of small size every time the view number varies.

15. The X-ray CT apparatus according to claim 14, wherein the reconstructing part is configured to:
reconstruct a first image based on the projection data obtained by detecting the X-ray radiated for the view number for the focal point size of large size;
reconstruct a second image based on the projection data obtained by detecting the X-ray radiated for the view number for the focal point size of small size; and
reconstruct a third image based on the projection data obtained by detecting the X-ray radiated for the view number for the focal point sizes of large size and small size.

16. The X-ray CT apparatus according to claim 15, further comprising a manipulation part configured to input selection of any of the first to third images, wherein the reconstructing part is configured to selectively reconstruct any of the first toward third images based on the input by the manipulation part.

17. The X-ray CT apparatus of claim 13, wherein the controller is configured to change the focal point size from a large size to a small size when the parameter is included within the reference range and change the focal point size from a small size to a large size when the parameter is out of the reference range.

18. An X-ray CT method to reconstruct an image from projection data obtained in a scan by radiation and detection of an X-ray, the X-ray CT method comprising:
setting an imaging condition for a real scan or a prep scan, which is scanning by a resolution lower than the real scan;
radiating an X-ray from an X-ray tube having a filament, an anode, and generators arranged opposite to each other across a path heading from the filament to the anode and configured to output an electric field or a magnetic field onto the path to focus an electron beam heading from the filament to the anode in accordance with the output under the imaging condition set in the setting step;
detecting the X-ray radiated from the X-ray tube;
reconstructing an image from the projection data based on the detected X-ray;
acquiring a CT value from the image reconstructed in the reconstructing step;
determining whether the CT value is included within a reference range; and
controlling an intensity of the output of the generators with reference to a result of the determining step to change a focal point size of the electron beam to a different size depending on the imaging condition during the scan, while continuously switching the scan between the prep scan and the real scan and changing the focal point size.

19. An X-ray CT method to reconstruct an image from projection data obtained in a scan by radiation and detection of an X-ray, the X-ray CT method comprising:
radiating an X-ray from an X-ray tube having a filament, an anode, and generators arranged opposite to each other across a path heading from the filament to the anode and configured to output an electric field or a magnetic field onto the path to focus an electron beam heading from the filament to the anode in accordance with the output;
detecting the X-ray radiated from the X-ray tube;
reconstructing an image from the projection data based on the detecting X-ray;
acquiring a parameter indicating a status of the scan, which is a value indicating a radiation position of the X-ray to a subject;
determining whether the parameter acquired in the acquiring step during the scan is included within a reference range that is a positional section in a radiation range of the X-ray into sections; and
controlling an intensity of the output of the generators with reference to a result of the determination in the determining step to change a focal point size of the electron beam to a different size depending on the determination result during the scan, while continuously changing the radiation position of the X-ray within the radiation range and changing the focal point size for each of the sections that the radiation position of the X-ray reaches.

20. An X-ray CT method performed by an X-ray CT apparatus connected to an electrocardiograph configured to acquire an electrocardiographic waveform of a subject so as to be capable of data communication, the X-ray CT apparatus configured to reconstruct an image from projection data obtained in a scan by radiation and detection of an X-ray, the X-ray CT method comprising:
radiating an X-ray from an X-ray tube having a filament, an anode, and generators arranged opposite to each other across a path heading from the filament to the anode and configured to output an electric field or a magnetic field onto the path to focus an electron beam heading from the filament to the anode in accordance with the output;

detecting the X-ray radiated from the X-ray tube;

reconstructing an image from the projection data based on the detected X-ray;

acquiring the electrocardiographic waveform from the electrocardiograph;

determining whether the electrocardiographic waveform acquired in the acquiring step during the scan is a specific waveform indicating a specific cardiac phase; and controlling an intensity of the output of the generators with reference to a result of the determination in the determining step to change a focal point size of the electron beam to a different size depending on the determination result during the scan, in synchronization with an appearance of the specific waveform from a waveform outputted from the electrocardiograph.

21. An X-ray CT method to reconstruct an image from projection data obtained in a scan by radiation and detection of an X-ray, the X-ray CT method comprising:

radiating an X-ray from an X-ray tube having a filament, an anode, and generators arranged opposite to each other across a path heading from the filament to the anode and configured to output an electric field or a magnetic field onto the path to focus an electron beam heading from the filament to the anode in accordance with the output;

detecting the X-ray radiated from the X-ray tube;

reconstructing an image from the projection data based on the detected X-ray;

acquiring a parameter indicating a view number of the X-ray radiation;

determining whether the parameter acquired in the acquiring step during the scan is included within a reference range; and controlling an intensity of the output of the generators with reference to a result of the determination in the determining step to change a focal point size of the electron beam to a different size for every view number during the scan.

\* \* \* \* \*